(12) United States Patent
Chu

(10) Patent No.: US 10,271,937 B2
(45) Date of Patent: *Apr. 30, 2019

(54) INSERTION DEVICE AND METHOD FOR DELIVERY OF A MESH CARRIER

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 217 days.

This patent is subject to a terminal disclaimer.

(21) Appl. No.: 15/069,499

(22) Filed: Mar. 14, 2016

(65) Prior Publication Data

US 2016/0193025 A1 Jul. 7, 2016

Related U.S. Application Data

(63) Continuation of application No. 13/888,892, filed on May 7, 2013, now Pat. No. 9,289,204, which is a
(Continued)

(51) Int. Cl.
*A61B 17/04* (2006.01)
*A61B 17/06* (2006.01)
(Continued)

(52) U.S. Cl.
CPC ........ *A61F 2/0045* (2013.01); *A61B 17/0401* (2013.01); *A61B 17/06109* (2013.01);
(Continued)

(58) Field of Classification Search
CPC .............. A61B 17/041; A61B 17/0469; A61B 17/06109; A61B 17/0625;
(Continued)

(56) References Cited

U.S. PATENT DOCUMENTS 527,263 A 10/1894 Blanchard
3,182,662 A 5/1965 Shirodkar
(Continued)

FOREIGN PATENT DOCUMENTS

DE 3223153 C1 8/1983
DE 4220283 A1 12/1993
(Continued)

OTHER PUBLICATIONS

International Search Report and Written Opinion received for PCT Patent Application No. PCT/US2009/040587, dated Oct. 21, 2009, 13 pages.
(Continued)

*Primary Examiner* — Julian W Woo
(74) *Attorney, Agent, or Firm* — Brake Hughes Bellermann LLP

(57) ABSTRACT

An insertion device includes an elongate member and a stylet. The elongate member has a proximal end portion, a distal end portion, and defines a lumen therethrough. The stylet has a proximal end portion, a distal end portion, and is slidably coupled to the elongate member. The stylet is configured to move from a first position to a second position with respect to the elongate member. The proximal end portion of the stylet is configured to removably couple a mesh carrier thereto. A portion of the proximal end portion of the stylet is disposed outside of the lumen of the elongate member when the stylet is in its first position and is disposed within the lumen when the stylet is in its second position.

20 Claims, 26 Drawing Sheets

Related U.S. Application Data continuation of application No. 12/549,704, filed on Aug. 28, 2009, now Pat. No. 8,449,573.

(60) Provisional application No. 61/120,105, filed on Dec. 5, 2008.

(51) Int. Cl.
*A61F 2/00* (2006.01)
*A61B 17/00* (2006.01)
*A61B 17/062* (2006.01)

(52) U.S. Cl.
CPC ........ *A61F 2/0022* (2013.01); *A61B 17/0469* (2013.01); *A61B 17/0625* (2013.01); *A61B 2017/00805* (2013.01); *A61B 2017/0409* (2013.01); *A61B 2017/0445* (2013.01); *A61B 2017/0464* (2013.01)

(58) Field of Classification Search
CPC .. A61B 2017/00805; A61B 2017/0409; A61B 2017/0445; A61B 2017/0464; A61F 2/0022; A61F 2/0045
See application file for complete search history.

(56) References Cited

U.S. PATENT DOCUMENTS

| | | | |
|---|---|---|---|
| 3,212,502 A | 10/1965 | Myers | |
| 3,311,110 A | 3/1967 | Singerman et al. | |
| 3,372,695 A | 3/1968 | Beliveau et al. | |
| 3,472,232 A | 10/1969 | Earl | |
| 3,565,073 A | 2/1971 | Giesy | |
| 3,608,095 A | 9/1971 | Barry | |
| 3,704,712 A | 12/1972 | Giesy et al. | |
| 3,763,860 A | 10/1973 | Clarke | |
| 3,858,783 A | 1/1975 | Kapitanov et al. | |
| 3,924,633 A | 12/1975 | Cook et al. | |
| 4,037,603 A | 7/1977 | Wendorff | |
| 4,128,100 A | 12/1978 | Wendorff | |
| 4,221,212 A | 9/1980 | Miller | |
| 4,235,238 A | 11/1980 | Ogiu et al. | |
| 4,392,495 A | 7/1983 | Bayers | |
| 4,441,497 A | 4/1984 | Paudler | |
| 4,509,516 A | 4/1985 | Richmond | |
| 4,549,545 A | 10/1985 | Levy | |
| 4,583,540 A | 4/1986 | Malmin | |
| 4,735,615 A | 4/1988 | Uddo, Jr. et al. | |
| 4,798,193 A | 1/1989 | Giesy et al. | |
| 4,824,435 A | 4/1989 | Giesy et al. | |
| 4,872,451 A | 10/1989 | Moore et al. | |
| 4,946,467 A | 8/1990 | Ohi et al. | |
| 4,946,468 A | 8/1990 | Li | |
| 4,976,717 A | 12/1990 | Boyle | |
| 5,002,550 A | 3/1991 | Li | |
| 5,013,292 A | 5/1991 | Lemay | |
| 5,032,508 A | 7/1991 | Naughton et al. | |
| 5,064,435 A | 11/1991 | Porter | |
| 5,078,730 A | 1/1992 | Li et al. | |
| 5,080,667 A | 1/1992 | Chen et al. | |
| 5,084,058 A | 1/1992 | Li | |
| 5,085,661 A | 2/1992 | Moss | |
| 5,087,263 A | 2/1992 | Li | |
| 5,112,344 A | 5/1992 | Petros | |
| 5,149,329 A | 9/1992 | Richardson | |
| 5,152,749 A | 10/1992 | Giesy et al. | |
| 5,180,385 A | 1/1993 | Sontag | |
| 5,207,679 A | 5/1993 | Li | |
| 5,217,438 A | 6/1993 | Davis et al. | |
| 5,250,033 A | 10/1993 | Evans et al. | |
| 5,256,150 A | 10/1993 | Quiachon et al. | |
| 5,281,237 A | 1/1994 | Gimpelson | |
| 5,292,327 A | 3/1994 | Dodd et al. | |
| 5,312,422 A | 5/1994 | Trott | |
| 5,334,185 A | 8/1994 | Giesy et al. | |
| 5,337,736 A | 8/1994 | Reddy | |
| 5,362,294 A | 11/1994 | Seitzinger | |
| 5,368,595 A | 11/1994 | Lewis | |
| 5,368,756 A | 11/1994 | Vogel et al. | |
| 5,382,257 A | 1/1995 | Lewis et al. | |
| 5,383,904 A | 1/1995 | Totakura et al. | |
| 5,395,349 A | 3/1995 | Ouiachon et al. | |
| 5,403,328 A | 4/1995 | Shallman | |
| 5,439,467 A | 8/1995 | Benderev et al. | |
| 5,441,508 A | 8/1995 | Gazielly et al. | |
| 5,450,860 A | 9/1995 | O'Connor | |
| 5,456,722 A | 10/1995 | McLeod et al. | |
| 5,499,991 A | 3/1996 | Garman et al. | |
| 5,505,735 A | 4/1996 | Li | |
| 5,507,796 A | 4/1996 | Hasson | |
| 5,520,700 A | 5/1996 | Beyar et al. | |
| 5,527,342 A | 6/1996 | Pietrzak et al. | |
| 5,540,703 A | 6/1996 | Barker, Jr. et al. | |
| 5,571,119 A | 11/1996 | Atala | |
| 5,582,188 A | 12/1996 | Benderev et al. | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,645,589 A | 7/1997 | Li | |
| 5,683,418 A | 11/1997 | Luscombe et al. | |
| 5,690,649 A | 11/1997 | Li | |
| 5,702,215 A | 12/1997 | Li | |
| 5,741,299 A | 4/1998 | Rudt | |
| 5,742,943 A | 4/1998 | Chen | |
| 5,749,884 A | 5/1998 | Benderev et al. | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,860,993 A | 1/1999 | Thompson et al. | |
| 5,891,168 A | 4/1999 | Thal | |
| 5,899,906 A | 5/1999 | Schenk | |
| 5,899,909 A | 5/1999 | Claren et al. | |
| 5,899,999 A | 5/1999 | De Bonet | |
| 5,931,855 A | 8/1999 | Buncke | |
| 5,934,283 A | 8/1999 | Willem et al. | |
| 5,935,122 A | 8/1999 | Fourkas et al. | |
| 5,945,122 A | 8/1999 | Abra et al. | |
| 5,954,057 A | 9/1999 | Li | |
| 5,984,933 A | 11/1999 | Yoon | |
| 5,997,554 A | 12/1999 | Thompson | |
| 6,010,447 A | 1/2000 | Kardjian | |
| 6,030,393 A | 2/2000 | Corlew | |
| 6,039,686 A | 3/2000 | Kovac | |
| 6,042,534 A | 3/2000 | Gellman et al. | |
| 6,050,937 A | 4/2000 | Benderev | |
| 6,053,935 A | 4/2000 | Brenneman et al. | |
| 6,096,041 A | 8/2000 | Gellman et al. | |
| 6,099,547 A | 8/2000 | Gellman et al. | |
| 6,110,101 A | 8/2000 | Tihon et al. | |
| 6,117,067 A | 9/2000 | Gil-Vernet | |
| 6,200,330 B1 | 3/2001 | Benderev et al. | |
| 6,221,005 B1 | 4/2001 | Bruckner et al. | |
| 6,221,084 B1 | 4/2001 | Fleenor | |
| 6,264,676 B1 | 7/2001 | Gellman et al. | |
| 6,273,852 B1 | 8/2001 | Lehe et al. | |
| 6,306,079 B1 | 10/2001 | Trabucco | |
| 6,306,156 B1 | 10/2001 | Clark | |
| 6,334,446 B1 | 1/2002 | Beyar | |
| 6,382,214 B1 | 5/2002 | Raz et al. | |
| 6,398,787 B1 | 6/2002 | Itoman | |
| 6,406,423 B1 | 6/2002 | Scetbon | |
| 6,423,072 B1 | 7/2002 | Zappala | |
| 6,423,080 B1 | 7/2002 | Gellman et al. | |
| 6,475,139 B1 | 11/2002 | Miller | |
| 6,478,727 B2 | 11/2002 | Scetbon | |
| 6,491,703 B1 | 12/2002 | Ulmsten | |
| 6,494,887 B1 | 12/2002 | Kaladelfos | |
| 6,530,943 B1 | 3/2003 | Hoepffner et al. | |
| 6,582,443 B2 | 6/2003 | Cabak et al. | |
| 6,596,001 B2 | 7/2003 | Stormby et al. | |
| 6,596,002 B2 | 7/2003 | Therin et al. | |
| 6,599,235 B2 | 7/2003 | Kovac | |

(56) References Cited

U.S. PATENT DOCUMENTS

| | | |
|---|---|---|
| 6,605,097 B1 | 8/2003 | Lehe et al. |
| 6,612,977 B2 | 9/2003 | Staskin et al. |
| 6,635,058 B2 | 10/2003 | Beyar et al. |
| 6,638,209 B2 | 10/2003 | Landgrebe |
| 6,638,210 B2 | 10/2003 | Berger |
| 6,638,211 B2 | 10/2003 | Suslian et al. |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,652,561 B1 | 11/2003 | Tran |
| 6,685,629 B2 | 2/2004 | Therin |
| 6,691,711 B2 | 2/2004 | Raz et al. |
| 6,730,110 B1 | 5/2004 | Harari et al. |
| 6,755,781 B2 | 6/2004 | Gellman |
| 6,802,807 B2 | 10/2004 | Anderson et al. |
| 6,830,052 B2 | 12/2004 | Carter et al. |
| 6,848,152 B2 | 2/2005 | Genova et al. |
| 6,932,759 B2 | 8/2005 | Kammerer et al. |
| 7,377,926 B2 | 5/2008 | Topper et al. |
| 7,381,212 B2 | 6/2008 | Topper et al. |
| 7,387,634 B2 | 6/2008 | Benderev |
| 7,524,281 B2 | 4/2009 | Chu et al. |
| 8,449,573 B2 | 5/2013 | Chu |
| 8,591,545 B2 | 11/2013 | Lunn et al. |
| 8,968,334 B2 | 3/2015 | Ostrovsky et al. |
| 9,011,489 B2 | 4/2015 | Ostrovsky et al. |
| 9,289,204 B2 * | 3/2016 | Chu ................ A61B 17/0401 |
| 2001/0018549 A1 | 8/2001 | Scetbon |
| 2001/0037119 A1 | 11/2001 | Schmieding |
| 2001/0049467 A1 | 12/2001 | Lehe et al. |
| 2002/0028980 A1 | 3/2002 | Thierfelder et al. |
| 2002/0058959 A1 | 5/2002 | Gellman |
| 2002/0072694 A1 | 6/2002 | Snitkin et al. |
| 2002/0077526 A1 | 6/2002 | Kammerer et al. |
| 2002/0091373 A1 | 7/2002 | Berger |
| 2002/0116025 A1 | 8/2002 | Haab |
| 2002/0120277 A1 | 8/2002 | Hauschild et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151910 A1 | 10/2002 | Gellman et al. |
| 2002/0161382 A1 | 10/2002 | Neisz et al. |
| 2002/0188169 A1 | 12/2002 | Kammerer et al. |
| 2002/0188301 A1 | 12/2002 | Dallara et al. |
| 2003/0004395 A1 | 1/2003 | Therin |
| 2003/0004580 A1 | 1/2003 | Sump et al. |
| 2003/0009181 A1 | 1/2003 | Gellman et al. |
| 2003/0010929 A1 | 1/2003 | Priewe et al. |
| 2003/0023135 A1 | 1/2003 | Ulmsten et al. |
| 2003/0023138 A1 | 1/2003 | Luscombe |
| 2003/0028075 A1 | 2/2003 | Ulmsten et al. |
| 2003/0050530 A1 | 3/2003 | Neisz et al. |
| 2003/0065336 A1 | 4/2003 | Xiao |
| 2003/0088272 A1 | 5/2003 | Smith |
| 2003/0100954 A1 | 5/2003 | Schuldt-Hempe et al. |
| 2003/0120309 A1 | 6/2003 | Colleran et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0171778 A1 | 9/2003 | Lizardi |
| 2003/0176762 A1 | 9/2003 | Kammerer |
| 2003/0195386 A1 | 10/2003 | Thierfelder et al. |
| 2003/0220538 A1 | 11/2003 | Jacquetin |
| 2004/0002734 A1 | 1/2004 | Fallin et al. |
| 2004/0039453 A1 | 2/2004 | Anderson et al. |
| 2004/0087978 A1 | 5/2004 | Velez et al. |
| 2004/0098053 A1 | 5/2004 | Tran |
| 2004/0106847 A1 | 6/2004 | Benderev |
| 2004/0237736 A1 | 12/2004 | Genova et al. |
| 2005/0203576 A1 | 9/2005 | Sulamanidze et al. |
| 2005/0228406 A1 | 10/2005 | Bose |
| 2006/0089525 A1 | 4/2006 | Mamo et al. |
| 2006/0173491 A1 | 8/2006 | Meade et al. |
| 2006/0217589 A1 | 9/2006 | Wan et al. |
| 2006/0229596 A1 | 10/2006 | Weiser et al. |
| 2006/0282161 A1 | 12/2006 | Huynh et al. |
| 2007/0016135 A1 | 1/2007 | Kanner et al. |
| 2007/0038249 A1 | 2/2007 | Kolster |
| 2007/0112384 A1 | 5/2007 | Conlon et al. |
| 2007/0129758 A1 | 6/2007 | Saadat |
| 2008/0103527 A1 | 5/2008 | Martin et al. |
| 2008/0132931 A1 | 6/2008 | Mueller |
| 2009/0076529 A1 | 3/2009 | Ganti |
| 2009/0287245 A1 | 11/2009 | Ostrovsky et al. |
| 2010/0268255 A1 | 10/2010 | Ostrovsky et al. |
| 2010/0324357 A1 | 12/2010 | Chu |
| 2011/0106108 A1 | 5/2011 | Ostrovsky et al. |
| 2013/0253259 A1 | 9/2013 | Chu |
| 2015/0148820 A1 | 5/2015 | Ostrovsky et al. |

FOREIGN PATENT DOCUMENTS

| | | |
|---|---|---|
| DE | 4334419 A1 | 4/1995 |
| DE | 10103179 A1 | 7/2001 |
| DE | 202007015955 U1 | 3/2009 |
| EP | 0598976 A2 | 6/1994 |
| EP | 0599772 A1 | 6/1994 |
| EP | 0688056 A1 | 12/1995 |
| EP | 0774240 A1 | 5/1997 |
| EP | 0941712 A1 | 9/1999 |
| EP | 1025811 A2 | 8/2000 |
| FR | 2422386 A1 | 11/1979 |
| JP | 2005-532848 A | 11/2005 |
| JP | 2006-515204 A | 5/2006 |
| JP | 2007-532174 A | 11/2007 |
| JP | 2007-535335 A | 12/2007 |
| SE | 503271 C2 | 4/1996 |
| SU | 1225547 A1 | 4/1986 |
| SU | 1443873 A1 | 12/1988 |
| WO | 1990/003766 A1 | 4/1990 |
| WO | 1996/006567 A1 | 3/1996 |
| WO | 1996/006597 A1 | 3/1996 |
| WO | 1997/013465 A1 | 4/1997 |
| WO | 1998/031301 A1 | 7/1998 |
| WO | 1998/034545 A1 | 8/1998 |
| WO | 2000/074594 A1 | 12/2000 |
| WO | 2001/006951 A1 | 2/2001 |
| WO | 2001/078609 A2 | 10/2001 |
| WO | 2002/026108 A2 | 4/2002 |
| WO | 2002/028312 A1 | 4/2002 |
| WO | 2002/038079 A2 | 5/2002 |
| WO | 2004/012626 A1 | 2/2004 |
| WO | 2004/112585 A2 | 12/2004 |
| WO | 2005/122954 A1 | 12/2005 |
| WO | 2006/108145 A1 | 10/2006 |
| WO | 2007/098212 A2 | 8/2007 |
| WO | 2008/020937 A2 | 2/2008 |
| WO | 2008/087635 A2 | 7/2008 |
| WO | 2009/140012 A1 | 11/2009 |
| WO | 2010-065274 A1 | 6/2010 |
| WO | 2010/121052 A2 | 10/2010 |

OTHER PUBLICATIONS

International Search Report and Written Opinion received for PCT Patent Application No. PCT/US2009/064564, dated Feb. 23, 2010, 13 pages.

International Search Report and Written opinion received for PCT Patent Application No. PCT/US2010/031273, dated Dec. 1, 2010, 17 pages.

International Preliminary Report on Patentability received for PCT Patent Application No. PCT/US2009/040587, dated Nov. 25, 2010, 10 pages.

International Preliminary Report on Patentability received for PCT Patent Application No. PCT/US2009/064564, dated Jun. 16, 2011, 9 pages.

Restriction Requirement received for U.S. Appl. No. 12/394,965, dated May 18, 2011, 6 pages.

Response to Restriction Requirement for U.S. Appl. No. 12/394,965, filed Jun. 15, 2011, 1 page.

Non-Final Office Action received for U.S. Appl. No. 12/394,965, dated Aug. 8, 2011, 15 pages.

(56) References Cited

OTHER PUBLICATIONS

Response to Non-Final Office Action for U.S. Appl. No. 12/394,965, filed Nov. 3, 2011, 11 pages.
Non-Final Office Action received for U.S. Appl. No. 12/394,965, dated Mar. 2, 2012, 13 pages.
Response to Non-Final Office Action for U.S. Appl. No. 12/394,965, filed Jun. 4, 2012, 9 pages.
Final Office Action received for U.S. Appl. No. 12/394,965, dated Dec. 7, 2012, 15 pages.
Response to Final Office Action for U.S. Appl. No. 12/394,965, filed Mar. 5, 2013, 24 pages.
Non-Final Office Action received for U.S. Appl. No. 12/394,965, dated Mar. 21, 2013, 14 pages.
Response to Non-Final Office Action for U.S. Appl. No. 12/394,965, filed Jul. 17, 2013, 12 pages.
Final Office Action received for U.S. Appl. No. 12/394,965, dated Oct. 31, 2013, 13 pages.
Response to Final Office Action for U.S. Appl. No. 12/394,965, filed Jan. 31, 2014, 14 pages.
Notice of Allowance received for U.S. Appl. No. 12/394,965, filed Dec. 17, 2014, 8 pages.
Non-Final Office Action received for U.S. Appl. No. 12/549,704, dated Sep. 26, 2011, 13 pages.
Response to Non-Final Office Action for U.S. Appl. No. 12/549,704, filed Dec. 23, 2011, 27 pages.
Final Office Action received for U.S. Appl. No. 12/549,704, dated Jan. 30, 2012, 30 pages.
Response to Final Office Action for U.S. Appl. No. 12/549,704, filed Apr. 27, 2012, 13 pages.
Non-Final Office Action received for U.S. Appl. No. 12/549,704, dated Jul. 25, 2012, 10 pages.
Response to Non-Final Office Action for U.S. Appl. No. 12/549,704, filed Oct. 25, 2012, 16 pages.
Final Office Action received for U.S. Appl. No. 12/549,704, dated Nov. 20, 2012, 12 pages.
Response to Final Office Action for U.S. Appl. No. 12/549,704, filed Jan. 18, 2013, 10 pages.
Notice of Allowance received for U.S. Appl. No. 12/549,704, dated Feb. 1, 2013, 10 pages.
Restriction Requirement received for U.S. Appl. No. 12/760,049, dated Mar. 29, 2012, 9 pages.
Response to Restriction Requirement for U.S. Appl. No. 12/760,049, filed Apr. 27, 2012, 4 pages.
Non-Final Office Action received for U.S. Appl. No. 12/760,049, dated Jun. 1, 2012, 17 pages.
Response to Non-Final Office Action for U.S. Appl. No. 12/760,049, filed Aug. 29, 2012, 18 pages.
Final Office Action received for U.S. Appl. No. 12/760,049, dated Nov. 8, 2012, 21 pages.
Response to Final Office Action for U.S. Appl. No. 12/760,049, filed Feb. 8, 2013, 22 pages.
Non-Final Office Action received for U.S. Appl. No. 12/760,049, dated Oct. 3, 2013, 19 pages.
Response to Non-Final Office Action for U.S. Appl. No. 12/760,049, filed Dec. 23, 2013, 10 pages.
Final Office Action received for U.S. Appl. No. 12/760,049, dated Apr. 4, 2014, 39 pages.
Response to Final Office Action for U.S. Appl. No. 12/760,049, filed May 28, 2014, 9 pages.
Non-Final Office Action received for U.S. Appl. No. 12/760,049, dated Jun. 19, 2014, 22 pages.
Response to Non-Final Office Action for U.S. Appl. No. 12/760,049, filed Sep. 17, 2014, 9 pages.
Notice of Allowance received for U.S. Appl. No. 12/760,049, dated Oct. 24, 2014, 7 pages.
Restriction Requirement received for U.S. Appl. No. 12/938,553, dated Dec. 28, 2012, 9 pages.
Response to Restriction Requirement for U.S. Appl. No. 12/938,553, filed Jan. 25, 2013, 8 pages.

Non-Final Office Action received for U.S. Appl. No. 12/938,553, dated Jun. 7, 2013, 8 pages.
Response to Non-Final Office Action for U.S. Appl. No. 12/938,553, filed Sep. 3, 2013, 15 pages.
Non-Final Office Action received for U.S. Appl. No. 12/938,553, dated Dec. 19, 2013, 9 pages.
Response to Non-Final Office Action for U.S. Appl. No. 12/938,553, filed Mar. 17, 2014, 8 pages.
Final Office Action received for U.S. Appl. No. 12/938,553, dated Aug. 6, 2014, 8 pages.
Response to Final Office Action for U.S. Appl. No. 12/938,553, filed Sep. 30, 2014, 7 pages.
Advisory Action received for U.S. Appl. No. 12/938,553, dated Oct. 21, 2014, 2 pages.
Non Final Office Action received for U.S. Appl. No. 12/938,553, dated Jan. 14, 2015, 11 pages.
Response to Non-Final Office Action for U.S. Appl. No. 12/938,553, filed Apr. 14, 2015, 10 pages.
Final Office Action received for U.S. Appl. No. 12/938,553, dated Jul. 27, 2015, 8 pages.
Notice of Allowance received for U.S. Appl. No. 12/938,553, dated Jul. 27, 2015, 8 pages.
Non-Final Office Action received for U.S. Appl. No. 13/888,892, dated Jul. 15, 2015, 11 pages.
Response to Non-Final Office Action for U.S. Appl. No. 13/888,892, filed Oct. 14, 2015, 9 pages.
Notice of Allowance received for U.S. Appl. No. 13/888,892, dated Nov. 16, 2015, 9 pages.
First Examiner Report received for Australian Patent Application No. 2009322835, dated May 21, 2014, 3 pages.
Response to First Examiner's Report for Australian Patent Application No. 2009322835, filed on Feb. 5, 2015, 21 pages.
Non-Final Office Action received for Japanese Patent Application No. 2011-509522, dated May 22, 2013, 3 pages. (Official Copy only).
Non-Final Office Action received for Japanese Patent Application No. 2011-509522, dated Sep. 13, 2013, 2 pages. (Official Copy only).
Final Office Action received for Japanese Patent Application No. 2011-509522, dated Jun. 12, 2014, 3 pages. (3 pages Office Action + 4 pages English Translation).
Office Action received for Canadian Patent Application No. 2,745,401, dated Oct. 16, 2015, 4 pages.
Bayer et al., "A New Approach to Primary Strengthening of Colostomy with Marlex Mesh to Prevent Paracolostomy Hernia", Dec. 1986, 1 page.
Delorme, Emmanuel, "La Bandelette Trans-Obturatrice: Un Procede Mini-Invasif Pour Traiter l'incontinence Urinaire D'effort De La Femme", vol. 11, No. 6, 2001, pp. 1306-1313.
Fianu et al., "Absorbable Polyglactin Mesh for Retropubic Sling Operation in Female Urinary Stress Incontinence", vol. 16, No. 1, 1983, 1 page.
Gittes et al., "No-Incision Pubovaginal Suspension for Stress Incontinence", Journal of Urology, vol. 138, No. 3, Sep. 1987, 1 page.
Haab et al., "Feasibility of Outpatient Percutaneous Bladder Neck Suspension Under Local Anesthesia", vol. 50, No. 4, Oct. 1997, 1 page.
Kovac et al., "Pubic Bone Suburethral Stabilization Sling for Recurrent Urinary Incontinence", Obstetrics & Gynecology, vol. 89, No. 4, Apr. 1997, 1 page.
Norris et al., "Use of Synthetic Material in Sling Surgery: A Minimally Invasive Approach", Journal of Endourology, vol. 10, No. 3, Jun. 1996, 4 pages.
Petros et al., "An Integral Theory and Its Method for the Diagnosis and Management of Female Urinary Incontinence", Scandinavian Journal of Urology and Nephrology, 1993, pp. 1-93.
Petros, P., "An Integral Theory of Bladder Neck Opening, Closure and Urinary incontinence in the Female", 1991.
Petros, P. P., "Medium-Term Follow-up of the Intravaginal Slingplasty Operation Indicates Minimal Deterioration of Urinary Continence with Time", vol. 39, No. 3, Aug. 1999, 2 pages.

(56) References Cited

OTHER PUBLICATIONS

Petros, P., "The Intravaginal Slingplasty Operation, a Minimally Invasive Technique for Cure of Urinary Incontinence in the Female", vol. 36, No. 4, 1996, 2 pages.

Petros et al., "Urethral Pressure Increase on Effort Originates from Within the Urethra, and Continence from Musculovaginal Closure", Neurourology and Urodynamics, vol. 14, No. 4, 1995, pp. 346-350.

Petros, P. E., "Vault Prolapse I: Dynamic Supports of the Vagina", vol. 12, No. 5, 2001, pp. 292-295.

Raz et al., "Fascial Sling to Correct Male Neurogenic Sphincter Incompetence: The McGuire/Raz approach", Journal of Urology, vol. 139, No. 3, Mar. 1988, pp. 528-531.

Raz S., "Modified Bladder Neck Suspension for Female Stress Incontinence", Urology vol. 17, No. 1, Jan. 1981, pp. 82-85.

Raz et al., "Vaginal Wall Sling", The Journal of Urology vol. 141, No. 1, 1989, pp. 43-46.

Richardson, P. A., "Ambulatory Surgery for Urinary Incontinence and Vaginal Prolapse", Medical Journal of Australia vol. 161, No. 8, 1994, pp. 171-172.

Stamey, Thomas A., "Endoscopic Suspension of the Vesical Neck for Urinary Incontinence in Females", Annals of Surgery vol. 192, No. 4, Oct. 1980, pp. 465-471.

Stamey, Thomas A., "Endoscopic Suspension of the Vesical Neck for Urinary Incontinence", Gynecology & Obstetrics vol. 136, No. 4, 1973, pp. 547-554.

Staskin, D. R., "Sling Surgery for the Treatment of Female", Stress Incontinence vol. 5, No. 1, 1991, pp. 106-122.

Staskin et al., "The Gore-Tex Sling Procedure for Female Sphincteric Incontinence: Indications, Technique, and Results", World Journal of Urology, vol. 15, No. 5, Oct. 1997, pp. 295-299.

Ulmsten et al., "An Ambulatory Surgical Procedure under Local Anesthesia for Treatment of Female Urinary Incontinence", The International Urogynecology Journal vol. 7, No. 2, 1996, pp. 81-86.

Ulmsten, U., "An Introduction to Tension-Free Vaginal Tape (TVT)—A New Surgical Procedure for Treatment of Female Urinary Incontinence", 2001, pp. S3-S4.

Ulmsten, U., "Connective Tissue Factors in the Aetiology of Female Pelvic Disorders", vol. 22, No. 6, Dec. 1990, pp. 403.

Ulmsten et al., "Intravaginal Slingplasty", Zentralbl Gynakol vol. 116, 1994, pp. 398-404.

Ulmsten et al., "Intravaginal Slingplasty (IVS): An Ambulatory Surgical Procedure for Treatment of Female Urinary Incontinence", Scand J Urol Nephrol, vol. 29, No. 1, Mar. 1995, pp. 75-82.

Ulmsten et al., "Surgery for Female Urinary Incontinence", Current Opinion in Obstetrics & Gynecology, vol. 4, No. 3, 1992, pp. 456-462.

Ulmsten, U., "The Basic Understanding and Clinical Results of Tension-Free Vaginal Tape for Stress Urinary Incontinence", vol. 40, No. 4, 2001, pp. 269-273.

"Suture" Available online at <http://www.thefreedictionary.com/suture>, Retrieved on May 21, 2012, 3 pages.

Giberti, C., "TVT Tension-Free Vaginal Tape, Minimally Invasive Highly Effective Treatment for Female Stress Unrinary Incontinence", Urology, vol. 57, No. 4, 2001, pp. 666-669.

U.S. Appl. No. 10/359,406, filed Feb. 6, 2003, 90 pages.
U.S. Appl. No. 12/549,704, filed Aug. 28, 2009, 54 pages.
U.S. Appl. No. 60/356,697, filed Feb. 14, 2002, 70 pages.

\* cited by examiner

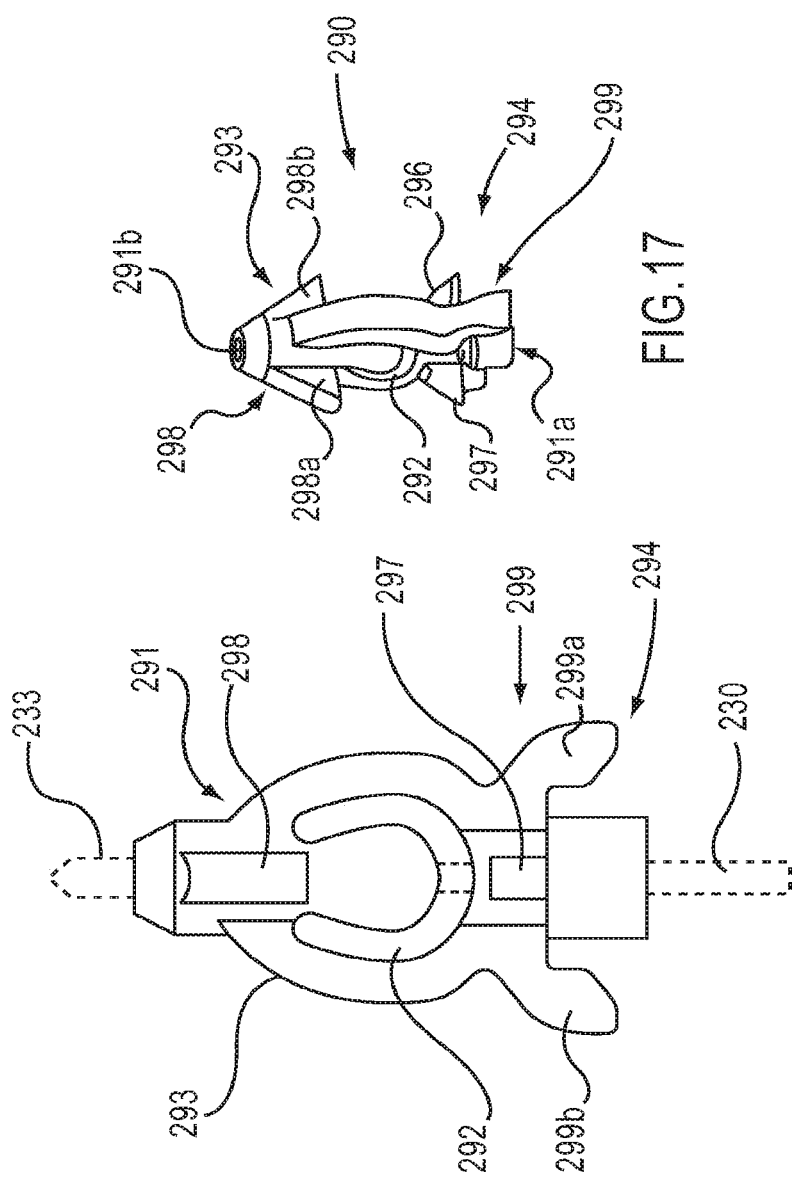

INSERTION DEVICE AND METHOD FOR DELIVERY OF A MESH CARRIER

CROSS-REFERENCE TO RELATED APPLICATIONS

This application is a continuation of, and claims priority to, U.S. patent application Ser. No. 13/888,892, filed on May 7, 2013, entitled "INSERTION DEVICE AND METHOD FOR DELIVERY OF A MESH CARRIER", now U.S. Pat. No. 9,289,204, which, in turn, claims priority to U.S. patent application Ser. No. 12/549,704, filed on Aug. 28, 2009, entitled "INSERTION DEVICE AND METHOD FOR DELIVERY OF A MESH CARRIER", now U.S. Pat. No. 8,449,573, which, in turn, claims priority to U.S. Provisional Patent Application No. 61/120,105, filed on Dec. 5, 2008, entitled "INSERTION DEVICE AND METHOD FOR DELIVERY OF A MESH CARRIER", the disclosures of which are incorporated by reference herein in their entirety.

BACKGROUND

The disclosed embodiments relate generally to medical devices and more particularly to an insertion device for delivery of a mesh carrier into a body of a patient.

The disclosed embodiments have application to a wide variety of surgical procedures. For example, one such procedure is directed to urinary incontinence and includes fixing an implant to tissue within a body of a patient to provide support for the urethra. Another such procedure includes fixing an implant to bodily tissue of a patient to support a bladder of the patient.

Mesh carriers may be placed within a body of a patient to provide anchoring points for medical implants. In some procedures, it is necessary for a practitioner, such as a physician, to insert a mesh carrier into bodily tissue of the patient at a location not easily visible or accessible to the practitioner. For example, some locations are not visible or easily accessible due to internal obstructions, such as the pubic bone. Known insertion devices can be used to position a mesh carrier at a first location within bodily tissue and to fix the mesh carrier to the tissue. However, in such procedures where the location is not easily visible or easily accessible, it may be difficult to maneuver the known insertion device around such obstructions and delivering the mesh carrier to a desired location in bodily tissue. Furthermore, the practitioner may require a larger incision at the incision site in order to allow ample room to rotate and/or pivot the known insertion device within the body in order to reach the desired location. In such an instance, the rotating and/or pivoting of the medical device may cause unintended stretching or tearing of tissue. Additionally, it may become necessary to remove the known insertion device from the body to better position it at the incision site. Unnecessary insertion, over-insertion, or excessive rotation could, therefore, induce trauma to the patient.

Thus, a need exists for an insertion device that has a configuration that facilitates insertion of an implant or a mesh carrier for an implant. For example, a need exists for an insertion device that facilitates insertion around or behind an internal obstruction, such as the pubic bone.

SUMMARY

In some embodiments, an insertion device includes an elongate member and a stylet. The elongate member has a proximal end portion, a distal end portion, and defines a lumen therethrough. The elongate member includes a curved portion between the proximal end portion and the distal end portion. In some embodiments, the distal end portion is configured to removably couple a mesh carrier thereto. The proximal end portion includes a handle defining a longitudinal axis. The stylet has a proximal end portion, a distal end portion, and is configured to move from a first position to a second position with respect to the elongate member. The stylet is configured to engage the mesh carrier to remove the mesh carrier from the elongate member such that a longitudinal axis defined by the mesh carrier is substantially orthogonal to the longitudinal axis defined by the handle.

In other embodiments, the elongate member has a proximal end portion, a distal end portion, and defines a lumen therethrough. The proximal end portion of the elongate member defines an axis substantially orthogonal to an axis defined by the distal end portion of the elongate member. The stylet has a proximal end portion and a distal end portion. At least a portion of the stylet is disposed within the lumen of the elongate member. The stylet is coupled to the elongate member such that the stylet is configured to move from a first position to a second position with respect to the elongate member.

BRIEF DESCRIPTION OF THE DRAWINGS

FIG. 16 is a side view of a mesh carrier according to an embodiment.

FIG. 17 is a perspective view of the mesh carrier of FIG. 16.

DETAILED DESCRIPTION

The insertion device and mesh carrier described herein can be inserted into a body of a patient, such as into bodily tissue. For example, the insertion device can be configured to deliver a first mesh carrier configured to selectively retain an implant (also referred to herein as a "filament", "tape", "implant", "mesh", "sling", or "strap") with respect to a bodily tissue. A plurality of such mesh carriers can be anchored within the body of a patient at spaced locations while retaining a filament between the plurality of mesh carriers to provide support for other portions of the body (e.g., organs or portions of organs).

The insertion device is configured to place, deposit, or otherwise insert a mesh carrier into a bodily tissue of a patient. The filament is configured to suspend or support a bodily tissue or organ when the filament is retained within the patient by one mesh carrier. Thus, in one embodiment, the insertion device can place the mesh carrier into the obturator externus muscle for incontinence treatment. Specifically, first and second mesh carriers are each placed in opposing obturator externus muscles of a patient and the filament is extended between the first and second mesh carriers to form a sling to provide support to the urethra or bladder neck of the patient. The insertion device can be a variety of different configurations and can have a variety of different components.

As used in this specification, the words "proximal" and "distal" refer to the direction closer to and further away from, respectively, an operator (e.g., surgeon, physician, nurse, technician, etc.) who would use an insertion device or a therapeutic device during a procedure. For example, the end of an insertion device first to contact the patient's body would be the distal end, while the opposite end of the insertion device (e.g., the end of the insertion device being operated by the operator) would be the proximal end of the insertion device. Similarly, the end of a insertion device implanted the furthest within the patient's body would be the distal end, while the opposite end of the insertion device (e.g., the end of the insertion device that is inserted the least amount within the body or the end of the insertion device that is disposed outside of the body) would be the proximal end.

Figure 1:
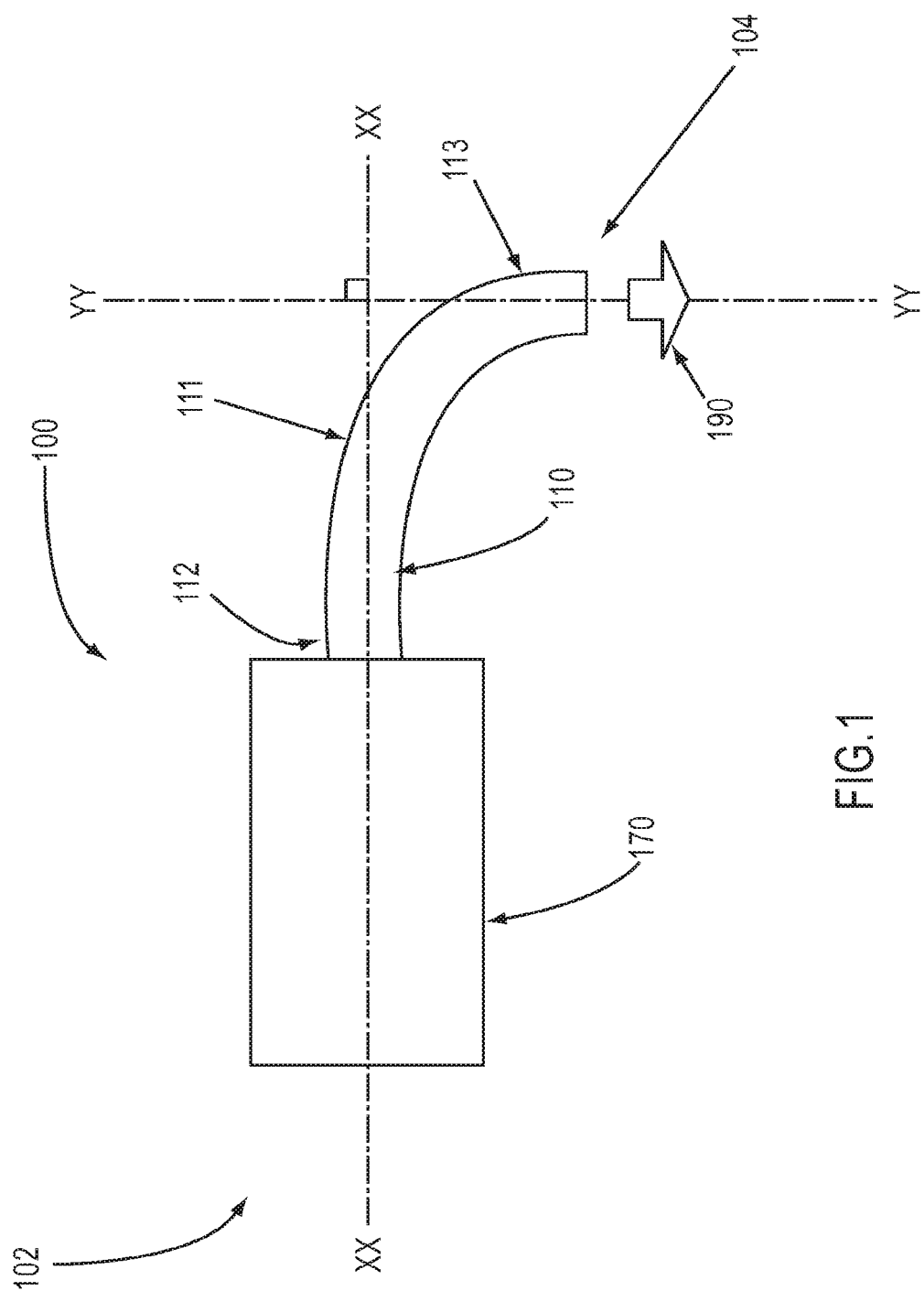
FIG. 1 is a schematic illustration of an insertion device according to one embodiment.
Figure 2:
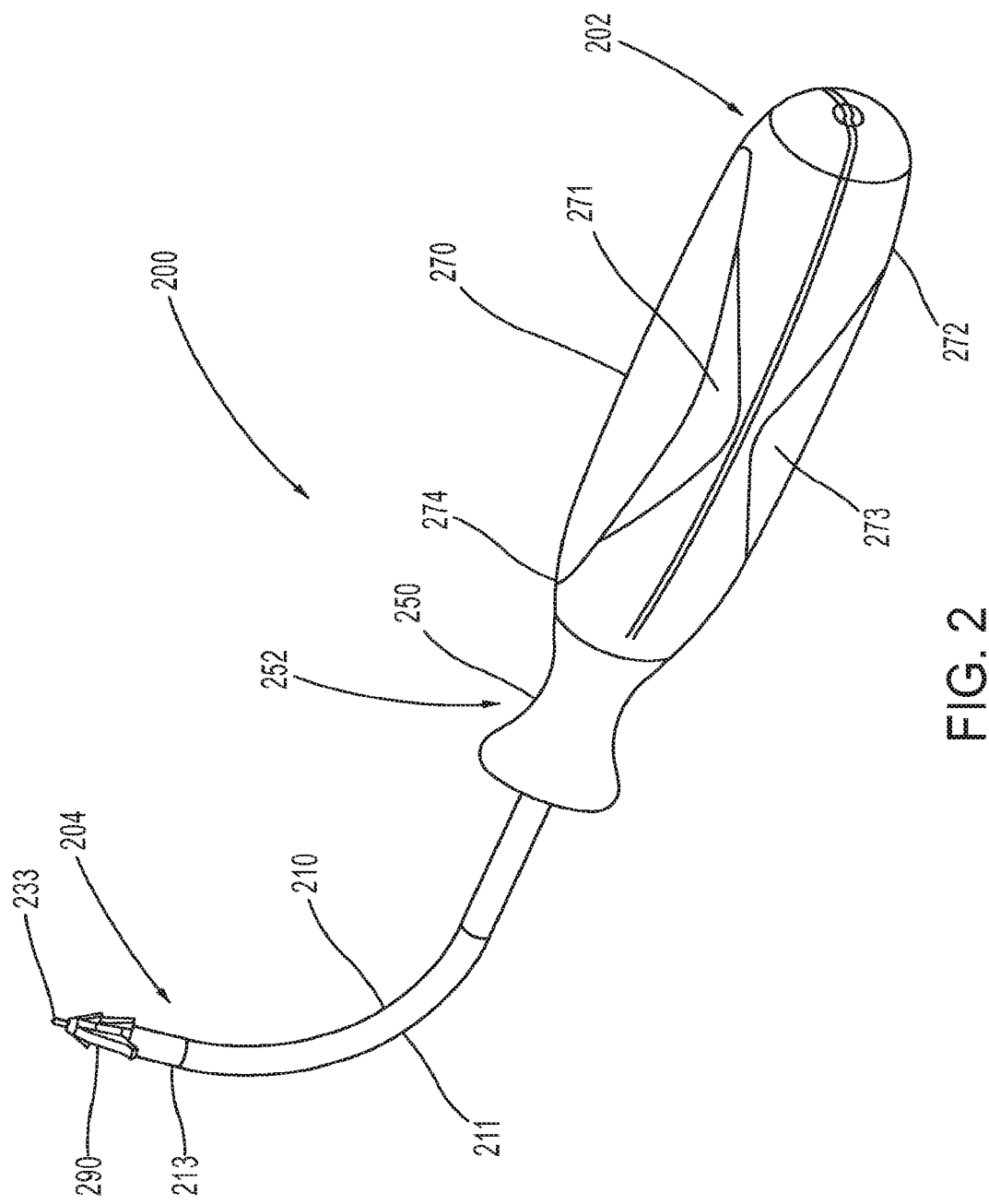
FIG. 2 is side perspective view of an insertion device coupled to a mesh carrier with a stylet in a first position according to another embodiment.

FIG. 1 is a schematic illustration of an insertion device 100 according to an embodiment of the invention. The insertion device 100 can be inserted into a body of a patient, such as into bodily tissue.

The insertion device 100 has a proximal end portion 102 and a distal end portion 104. The insertion device 100 includes an elongate member 110, a stylet (not shown in FIG. 1), and a handle 170. At least a portion of the elongate member 110 and the stylet are configured to be inserted into a body of a patient. The elongate member 110 includes a proximal end portion 112 and a distal end portion 113. In some embodiments, the proximal end portion 112 of the elongate member 110 is configured to be slidably coupled to the handle 170. The distal end portion 113 of the elongate member 110 is configured to be coupled to a mesh carrier 190. In some embodiments, the elongate member 110 includes a curved portion 111 between the proximal end portion 112 and the distal end portion 113. The curved portion 111 is configured such that an axis XX-XX defined by the proximal end portion 112 of the elongate member 110 is substantially orthogonal to an axis YY-YY defined by the distal end portion 113 of the elongate member 110 and is substantially orthogonal to a longitudinal axis defined by the mesh carrier 190 when the mesh carrier 190 is delivered into bodily tissue. In such embodiments, the curved portion 111 facilitates insertion of the device 100 around or behind an internal obstruction, such as the pubic bone, and allows more control when delivering the mesh carrier 190 into bodily tissue. Furthermore, curved portion 111 can define a radius of curvature of any suitable length. For example, the radius of curvature can be 1.0 inch, 1.1 inches, 1.5 inches, or 2 inches.

The handle 170 is slidably coupled to the proximal end portion 112 of the elongate member 110 and is fixedly coupled to the proximal end portion of the stylet. The handle 170 is configured to move the stylet relative to the elongate member 110.

Although a mesh carrier 190 is used with insertion device 100 as described in the above disclosed embodiment, it should be understood that in some embodiments, a tissue anchor can be used.

FIGS. 2-15, 18, and 19 illustrate one embodiment of an insertion device. Insertion device 200 includes a proximal end portion 202 and a distal end portion 204. The insertion device 200 includes an elongate member 210, a handle 270, and a stylet 230. The elongate member 210 and stylet 230 are configured to be at least partially inserted into a body of a patient.

The elongate member 210 includes a proximal end portion 212, a distal end portion 213, and defines a lumen 218 (shown, for example in FIGS. 5-10) extending therethrough. The lumen 218 is configured to receive at least a portion of the stylet 230.

As shown in FIGS. 2-5 and 9-14, the proximal end portion 212 of the elongate member 210 is coupled to a coupling member 250 and defines a first axis A-A. The coupling member 250 includes a distal end portion 252, a proximal end portion 254 (shown, for example, in FIGS. 3, 9, 10, 12, and 13), and defines a lumen therethrough (shown in FIGS. 12 and 13) configured to fixedly receive at least a portion of the elongate member 210. Thus, the coupling member 250 is configured to be fixedly disposed about the portion of the elongate member 210 and is configured to be moved such that the coupling member 250 moves the elongate member 210 relative to the stylet 230.

The distal end portion 252 of the coupling member 250 includes a first end portion 251, and second end portion 253 (shown, for example in FIGS. 2-5, 9-14). The second end portion 253 is configured to be disposed proximate a distal end portion 274 of the handle 270 when the stylet 230 is in a first position (shown, for example in FIGS. 2, 4, 11, and 12) and is configured to be spaced apart from the distal end portion 274 of the handle 270 when the stylet 230 is in a second position (shown, for example, in FIGS. 3 and 13).

Figure 10:
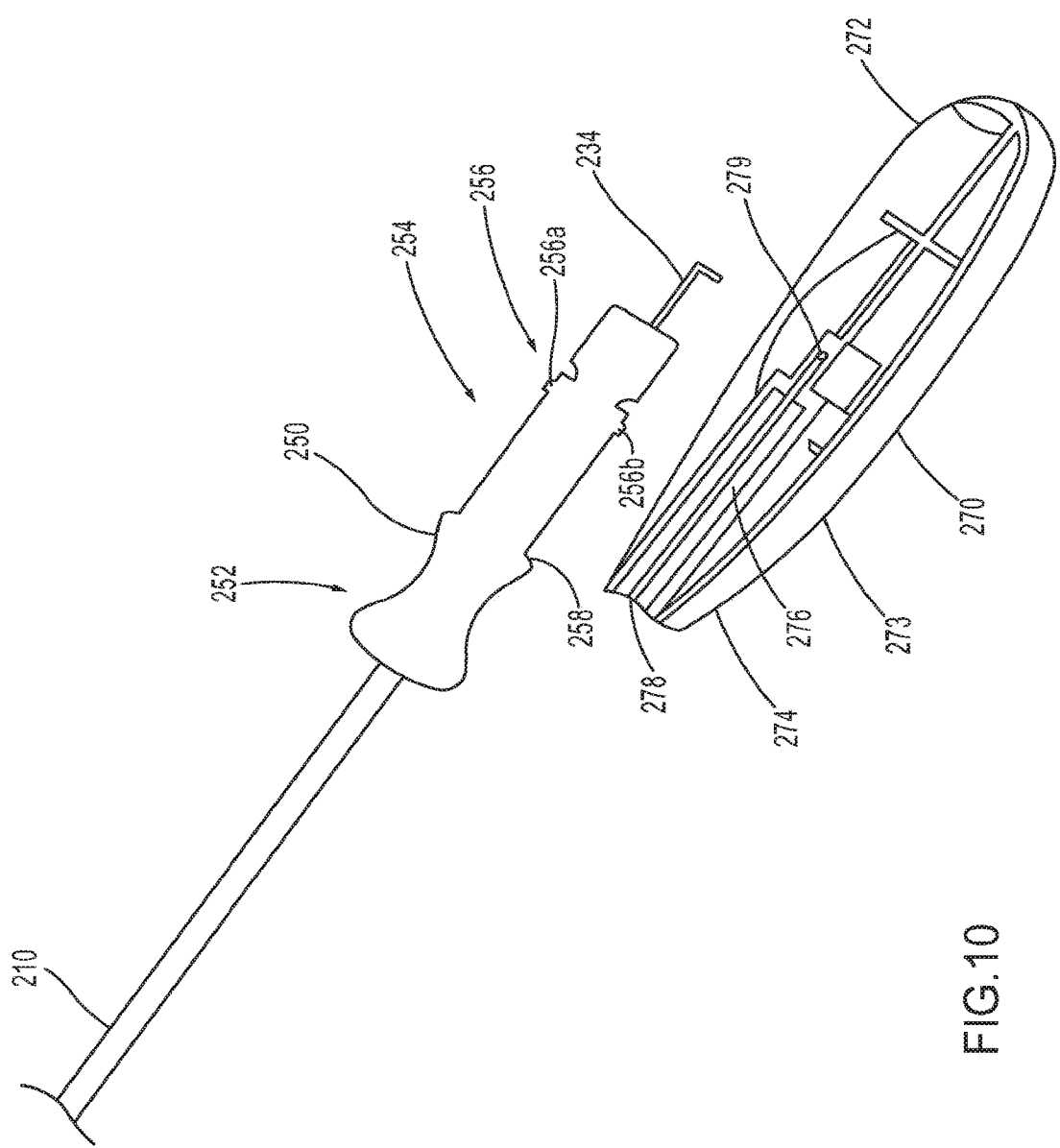
FIG. 10 is an exploded view of a portion of the insertion device of FIG. 2.
Figure 11:
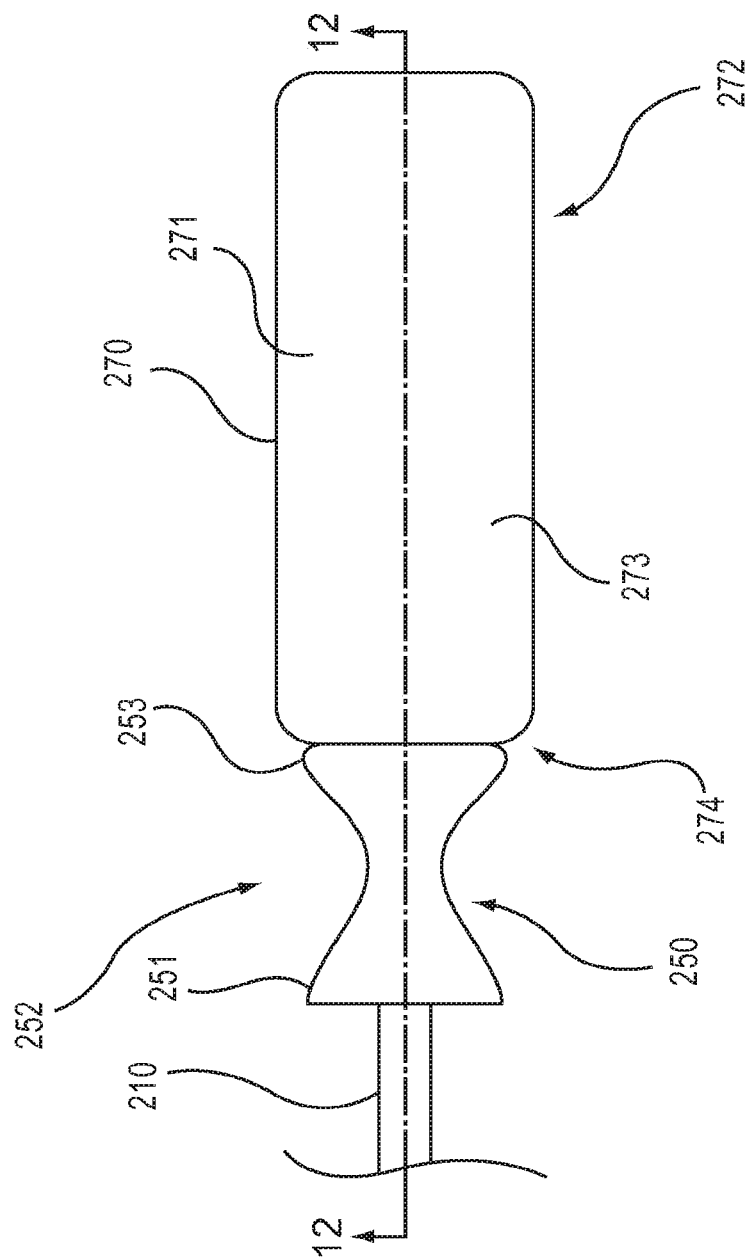
FIG. 11 is a side view of a portion of the insertion device of FIG. 2.
Figure 12:
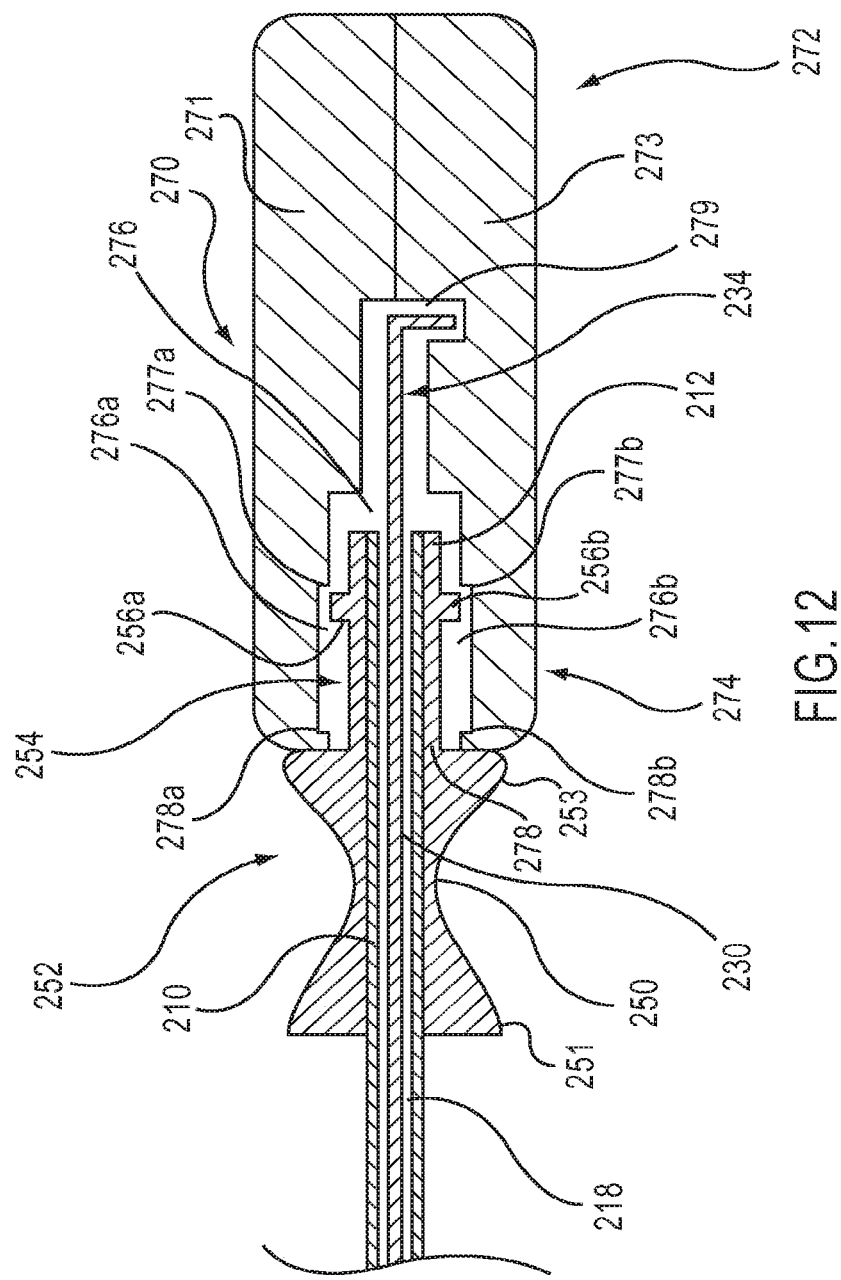
FIG. 12 is a cross-sectional view of the portion of the insertion device of FIG. 11 along line 12-12, with a stylet in a first position.
Figure 13:
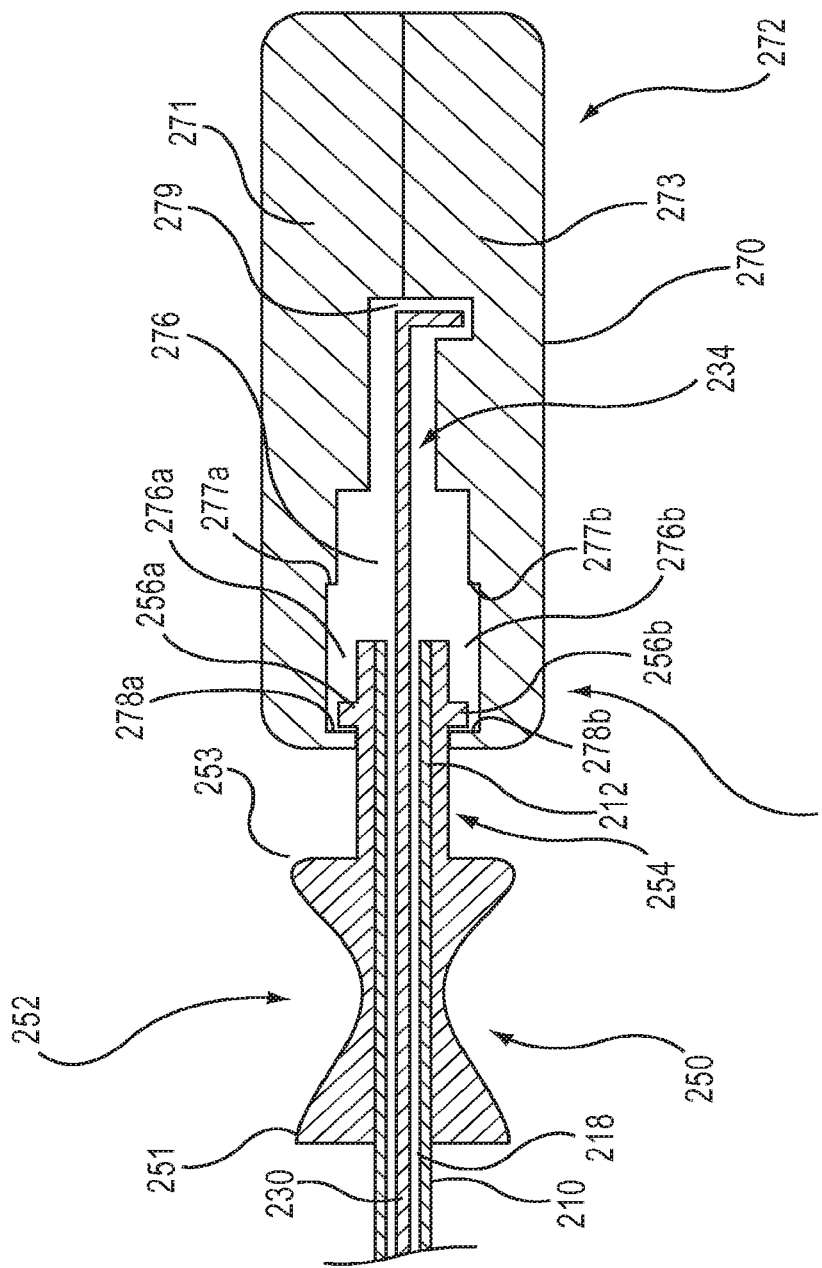
FIG. 13 is a cross-sectional view of the portion of the insertion device of FIG. 11 along line 12-12, with a stylet in a second position.
Figure 14:
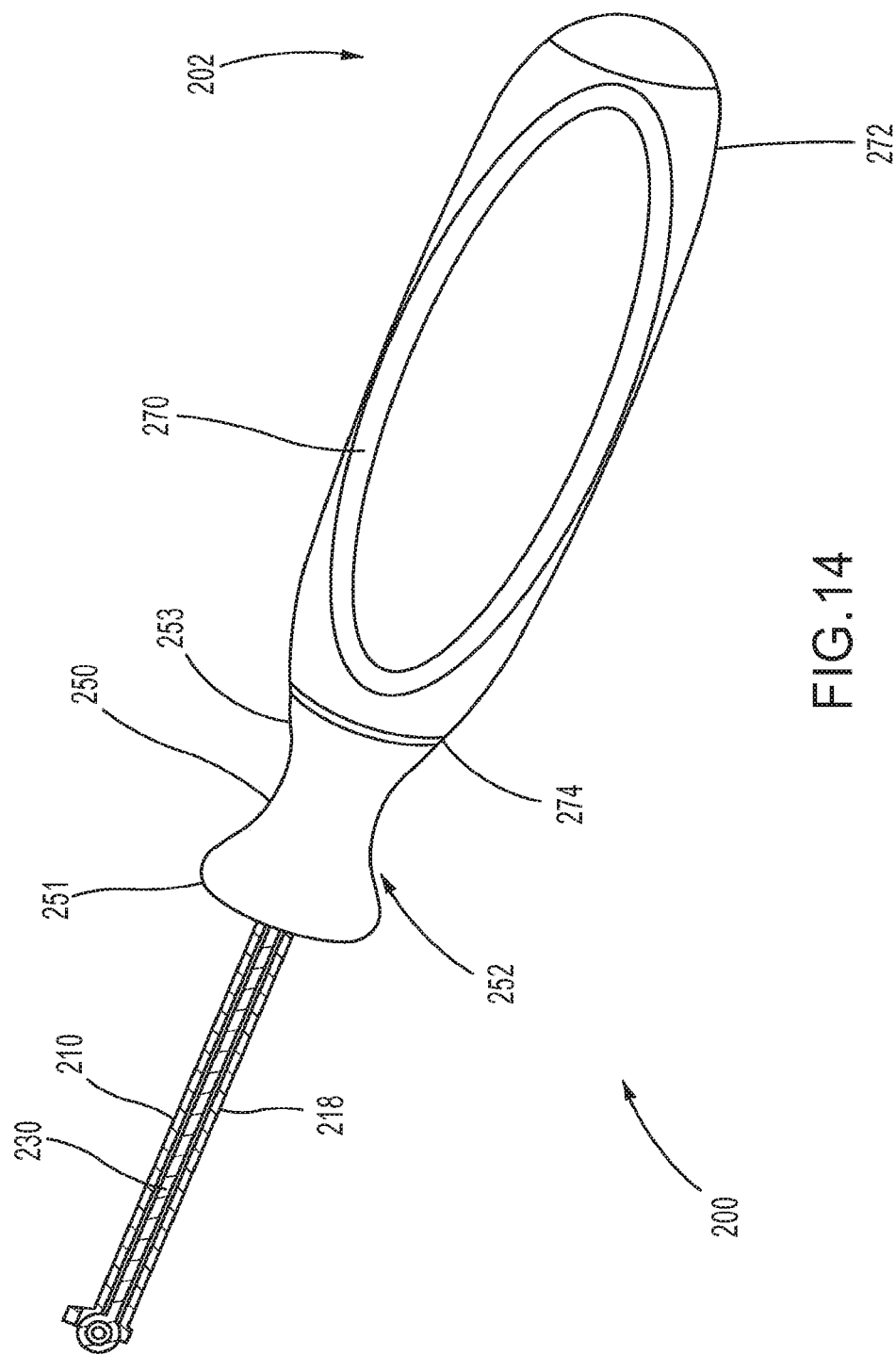
FIG. 14 is a bottom, partial cross-sectional view of the insertion device of FIG. 2.
Figure 15:
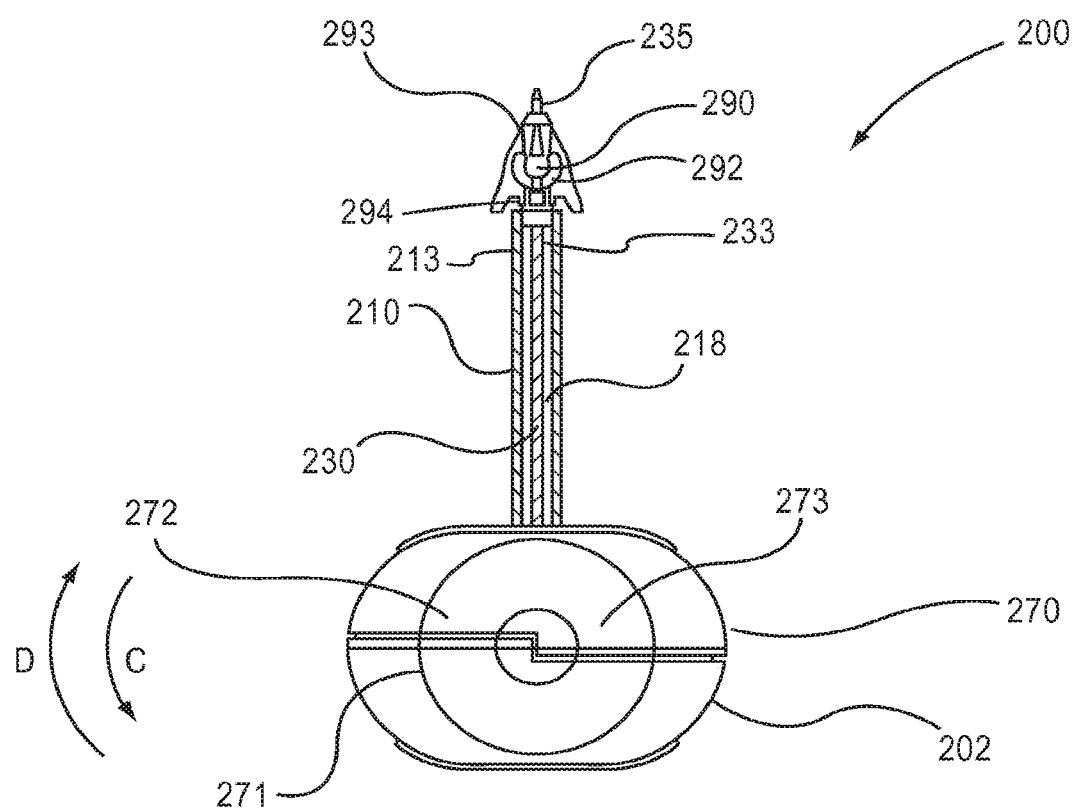
FIG. 15 is an end, partial cross-sectional view of the insertion device of FIG. 2.

The proximal end portion 254 of the coupling member 250 defines a ribbed portion 256 including a first protrusion 256a and a second protrusion 256b (shown in FIGS. 10, 12, and 13). At least a portion of the proximal end portion 254 is configured to be slidably disposed within a cavity 276 defined by the handle 270. Specifically, the ribbed portion 256 is configured to engage a groove portion of the handle 270 such that the coupling member 250 is slidably coupled to the handle 270 (discussed in detail below).

Although the coupling member 250 is illustrated and described as being disposed about or fixedly coupled to the elongate member 210, other suitable coupling configurations can be used. For example, in some embodiments, the coupling member 250 and elongate member 210 can be monolithically constructed. In other embodiments, for example, the coupling member 250 can be insert-molded to the elongate member 210. Furthermore, the coupling member 250 can be constructed of any suitable material. In one embodiment, the coupling member 250 can be constructed of a polymer. For example, the coupling member 250 can be constructed of acrylonitrile butadiene styrene (ABS).

Figure 5:
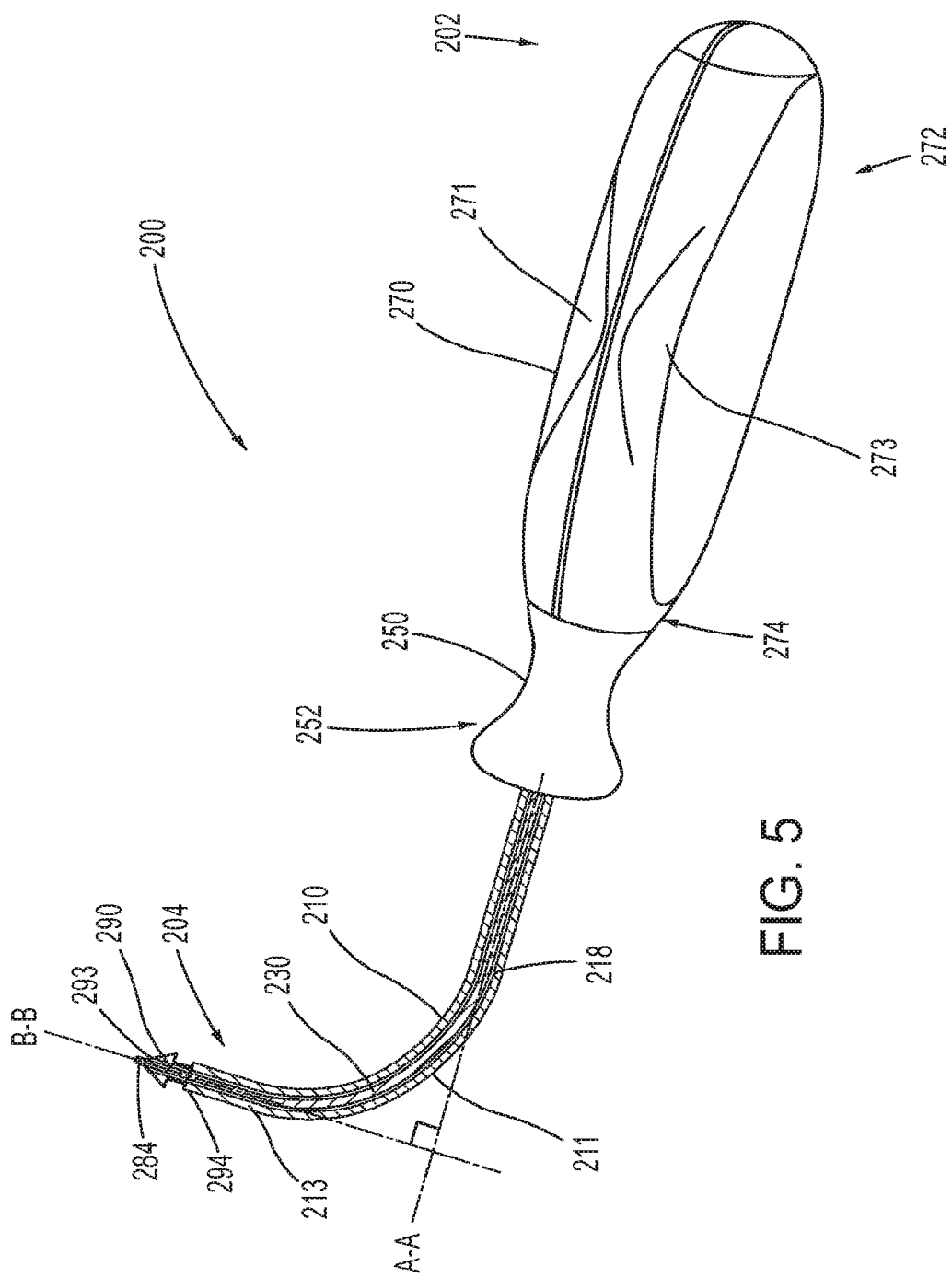
FIG. 5 is a partial cross-sectional view of the insertion device of FIG. 2.
Figure 6:
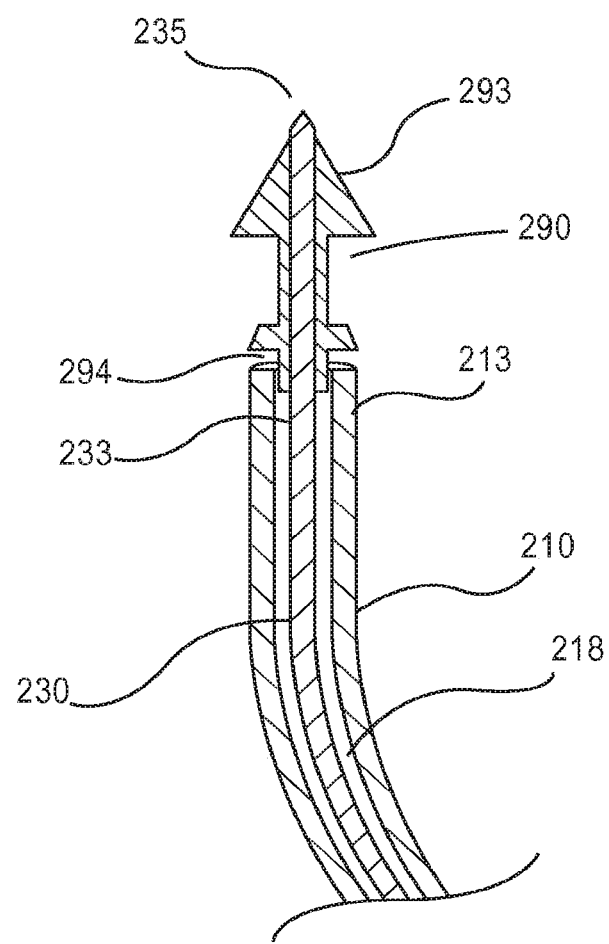
FIG. 6 is a cross-sectional view of a distal end portion of the insertion device of FIG. 2.
Figure 7:
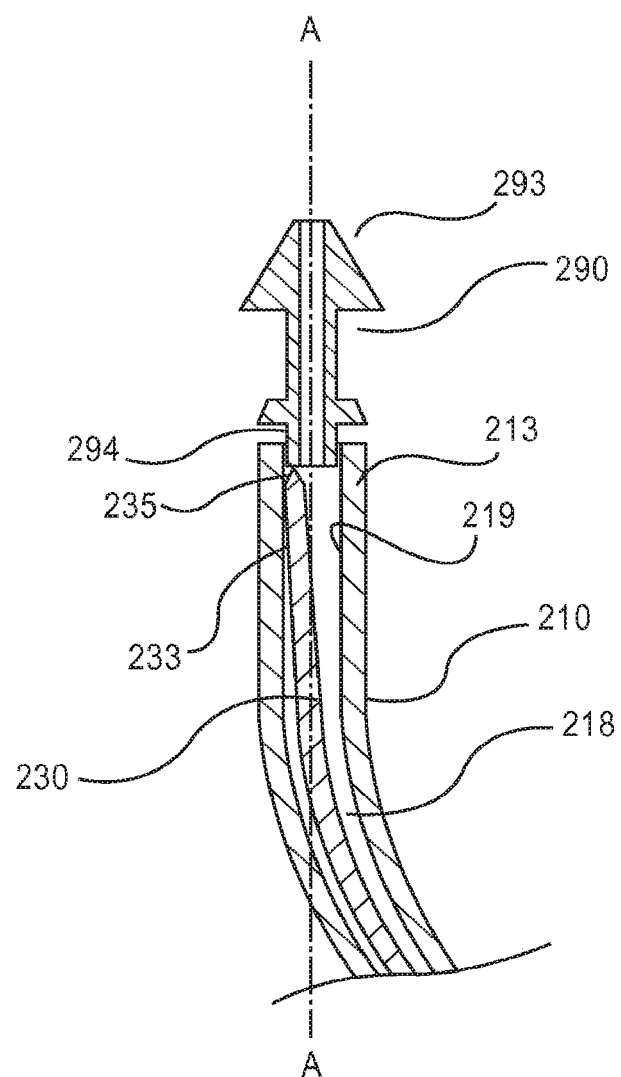
FIG. 7 is a cross-sectional view of a distal end portion of the insertion device of FIG. 3.
Figure 8:
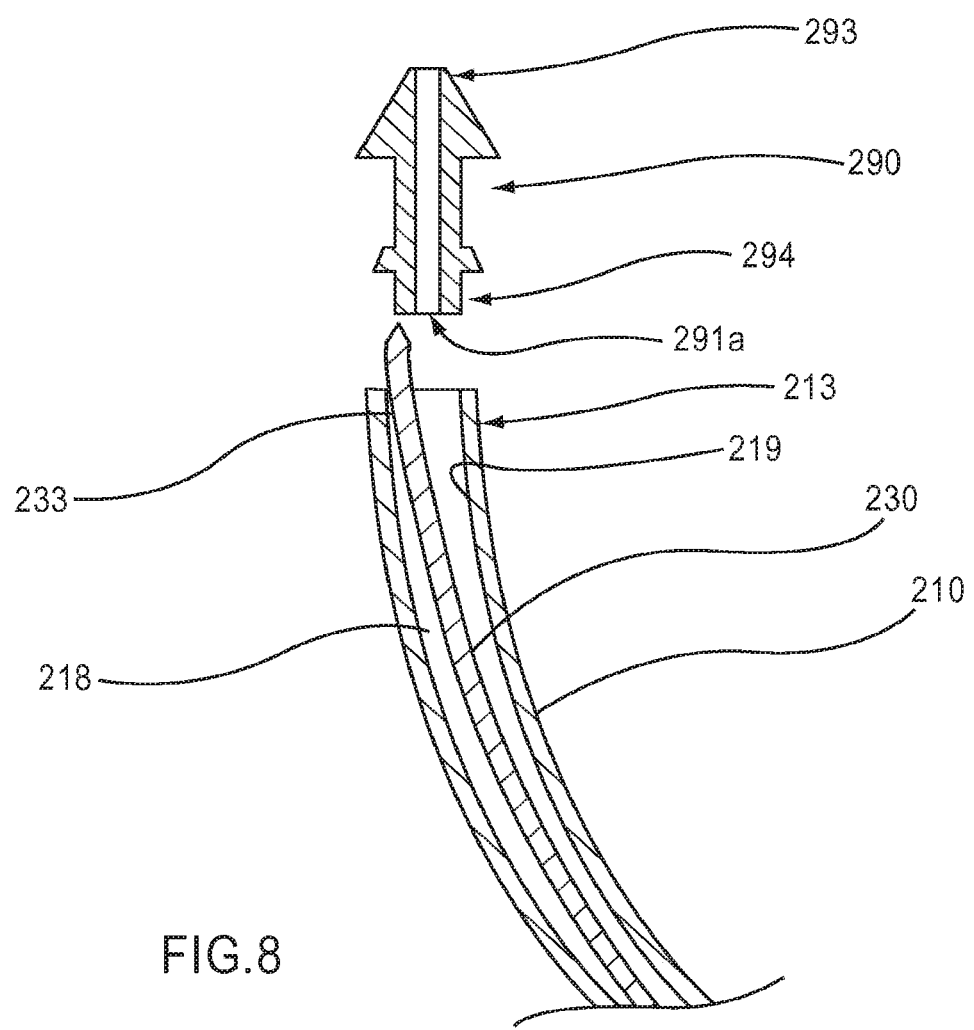
FIG. 8 is a cross-sectional view of a distal end portion of the insertion device of FIG. 2 removing the mesh carrier.
Figure 9:
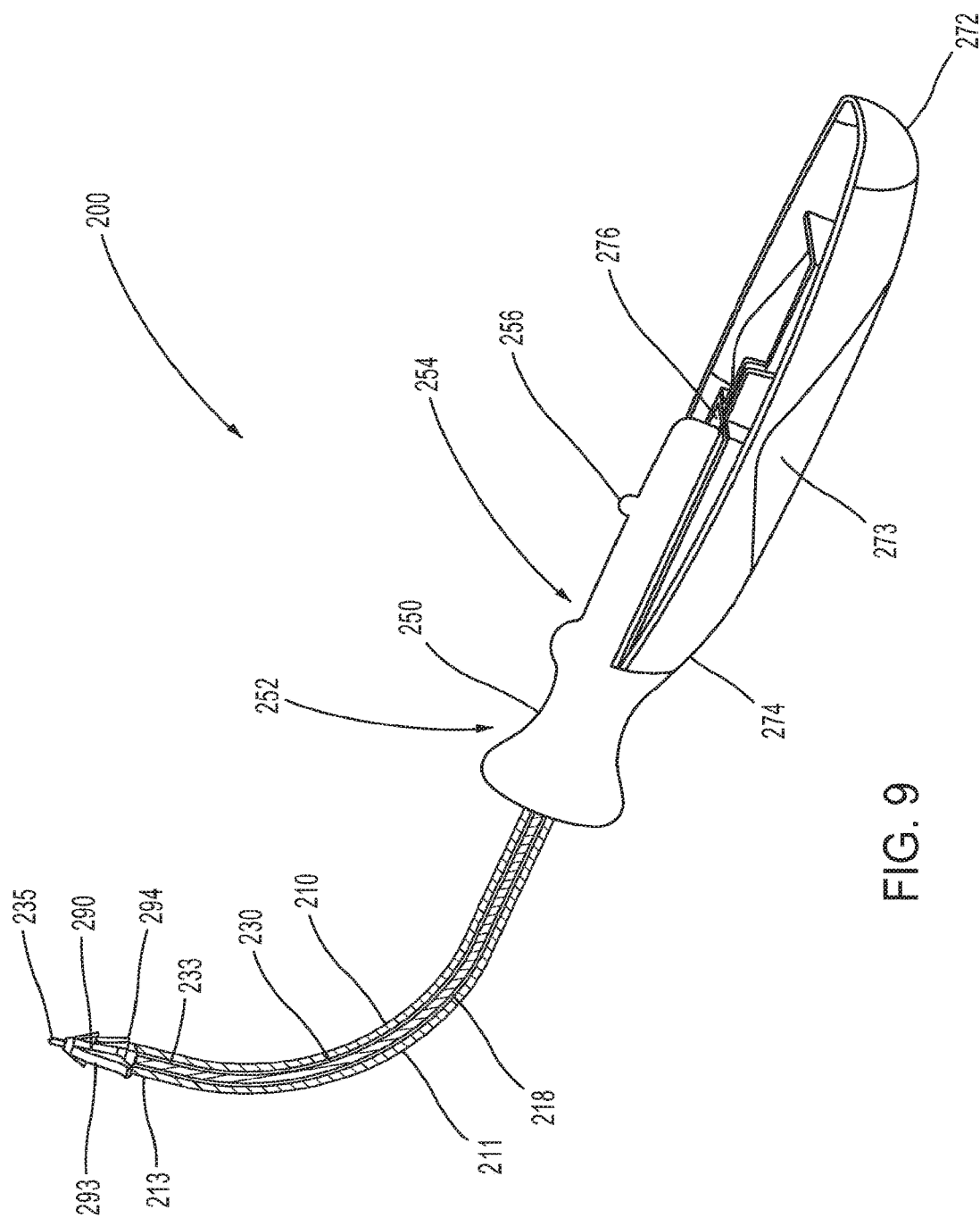
FIG. 9 is a partial cross-sectional view of the insertion device of FIG. 2 with a first portion of a handle removed.

The distal end portion 213 of the elongate member 210 defines a second axis B-B, as shown, for example in FIG. 5. The distal end portion 213 of the elongate member 210 is configured to interact with a proximal end portion 294 of a mesh carrier 290. In the illustrated embodiment, the distal end portion 213 of the elongate member 210 is configured to be removably coupled to the mesh carrier 290. Specifically, as shown in FIGS. 6 and 7, the lumen 218 defined by the distal end portion 213 is configured to receive at least a portion of the proximal end portion 294 of the mesh carrier 290 such that an inner surface 219 of the elongate member 210 defining the lumen 218 is configured to provide an interference or slight frictional fit with the proximal end portion 294 of the mesh carrier 290 received in the lumen 218.

The elongate member 210 includes a curved portion 211 disposed between the proximal end portion 212 and the distal end portion 213. Specifically, in the illustrated embodiment, the curved portion 211 is configured such that the second axis B-B defined by the distal end portion 213 of the elongate member is substantially orthogonal to the first axis A-A defined by the proximal end portion 212 of the elongate member 210.

The elongate member 210 can be constructed of any material suitable for insertion into a body of a patient. For example, in some embodiments, the elongate member is constructed of stainless steel. In other embodiments, the elongate member is constructed of a polymer.

The handle 270 has a proximal end portion 272 and a distal end portion 274, and is formed by a first portion (first half) 271, and a second portion (second half) 273. The handle defines a longitudinal axis B 1-B (shown in FIG. 4) and is configured to rotate about the longitudinal axis B1-B1 in a first direction C and a second direction D as shown, for example, in FIG. 15. The handle 270 is configured to be slidably coupled to the elongate member 210. The distal end portion 274 of the handle 270 is slidably coupled to the proximal end portion 212 of the elongate member 210 and is fixedly coupled to the proximal end portion 234 of the stylet 230.

As shown in FIGS. 2-5, the first portion 271 of the handle 270 is fixedly coupled to the second portion 273 of the handle 270 (not illustrated separately). The first and second portions 271, 273 can be coupled by any suitable coupling mechanisms. For example, the first and second portions 271, 273 can be coupled by an ultrasonic weld. The first portion 271 and the second portion 273 collectively define a cavity 276 configured to receive the elongate member 210. Specifically, in the illustrated embodiment, the distal end portion 274 of the handle 270 defines an opening 278 in communication with the cavity 276 for receiving at least a portion of the proximal end portion 212 of the elongate member 210 and the proximal end portion 254 of the coupling member 250.

As shown in FIGS. 12 and 13, the first portion 271 of the handle 270 defines a first groove portion 276a, a first wall portion 277a, and a second wall portion 278a. The first groove portion 276a is configured to slidably receive the first projection 256a of the ribbed portion 256 of the coupling member 250. The second portion 273 of the handle 270 defines a second groove portion 276b, a first wall portion 277b, and a second wall portion 278b. The second groove portion 276b is configured to slidably receive the second projection 256b of the ribbed portion 256 of the coupling member 250. The first wall portions 277a, 277b are configured to contact the projections 256a, 256b when the stylet 230 is in its first position (shown in FIG. 12). The second wall portions 278a, 278b are configured to contact the projections 256a, 256b when the stylet 230 is in its second position (shown in FIG. 13) to prevent removal of the coupling member 250 from the handle 270.

The second portion 272 of the handle 270 defines an aperture 279. The aperture 279 is configured to fixedly receive a portion of a proximal end portion 234 of the stylet 230 such that movement of the handle 270 with respect to the elongate member 210, causes the stylet 230 to slidably advance or retract relative to the elongate member 210.

Although the handle 270 is illustrated as defining a contoured shape (shown in FIGS. 2-5, and 11-14), the handle 270 can define a variety of shapes, sizes, and configurations, such as cylindrical shape. The handle 270 can further be constructed of any suitable material. In some embodiments, the handle 270 can be constructed of at least one polymer. For example, the handle 270 can be constructed of acrylonitrile butadiene styrene (ABS). In other embodiments, the handle 270 can include a thermoplastic elastomer material (TPE) covering a portion its outer surface to provide a practitioner a comfortable or secure gripping area.

The stylet 230 includes a proximal end portion 234 and a distal end portion 233. The stylet 230 is slidably disposed within the lumen 218 defined by the elongate member 210. The proximal end portion 234 is fixedly coupled to the handle 270. As shown in FIGS. 10, 12, and 13, the proximal end portion 234 of the stylet 230 includes an L-shaped portion configured to be received within the aperture 279 defined by the handle 270. Thus, as discussed above, movement of the handle 270 with respect to the elongate member 210, causes the stylet 230 to slidably advance or retract relative to the elongate member 210.

The distal end portion 233 of the stylet 230 includes a tip 235. The tip 235 can be a variety of shapes. For example, in one embodiment, the stylet tip can be pointed. In another embodiment, the stylet tip can be blunt or tapered.

Figure 3:
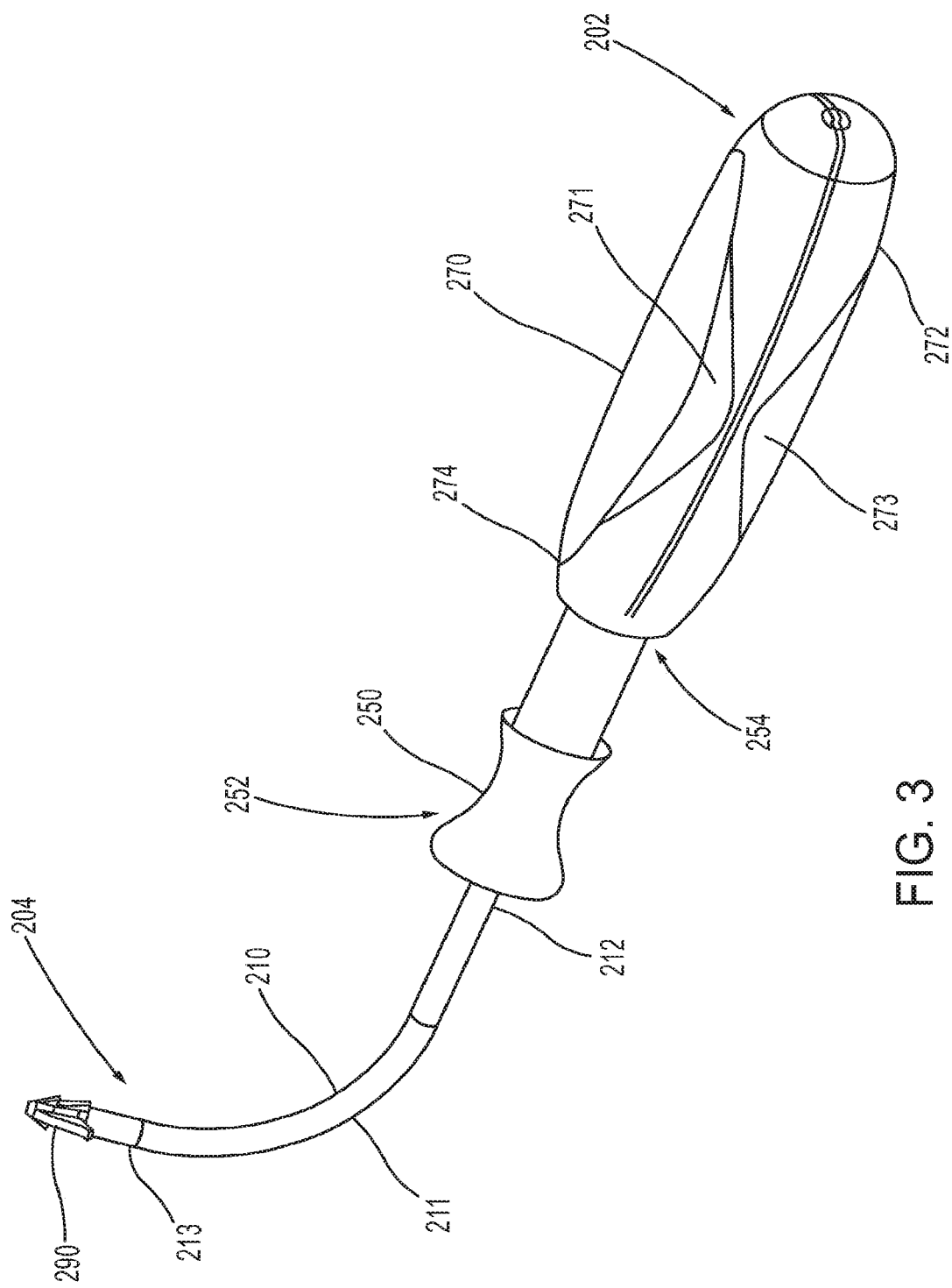
FIG. 3 is a side perspective view of the insertion device of FIG. 2 with the stylet in a second position.

The stylet 230 has a first position, (i.e., an extended position) shown, for example, in FIGS. 6, 12, 18, and 19, a second position (i.e., a retracted position), shown, for example in FIGS. 3, 7, and 13. The stylet is biased to a substantially linear configuration. When the stylet 230 is in its first position, at least a portion of the distal end portion 233 of the stylet 230 extends out of the lumen 218 at the distal end portion 213 of the elongate member 210. The portion of the distal end portion 233 is configured to extend through the lumen 291 and out of an opening 291 be defined by the mesh carrier (discussed in detail below). The portion of the distal end portion 233 is further configured to pierce and pass through a filament 205 received by the mesh carrier 290 (shown in FIGS. 18 and 19). Because the stylet 230 is biased to a substantially linear configuration, its engagement with mesh carrier 290 maintains its position within the center of the lumen 218 defined by the elongate member 210. Said another way, when the stylet 230 is in its first position, the interaction between the stylet 230 and the mesh carrier 290 results in the distal end portion 233 of the stylet 230 being disposed along the axis B-B defined by the distal end portion 213 of the elongate member 210 (shown, for example, in FIG. 5).

As the stylet 230 is moved proximally with respect to the elongate member 210 from its first position to its second position, the distal end portion 233 of the stylet is removed from the lumen 291 defined by the mesh carrier 290. When the stylet 230 is in its second position, the distal end portion 233 of stylet 230 is disposed within the lumen 218 of the elongate member 210. Because the stylet 230 is biased to a linear configuration, when it is in its second position and is no longer engaged with the mesh carrier 290, the distal end portion 233 of the stylet 230 is disposed substantially against the inner surface 219 of the elongate member 210 (shown, for example, in FIG. 7). Specifically, in the illustrated embodiment, when the stylet 230 is in its second position, the stylet 230 is disposed within the lumen 218 of the elongate member 210 such that the distal end portion 233 of the stylet 230 is offset from the axis B-B defined by the distal end portion 213 of the elongate member 210 (shown in FIG. 7).

In some embodiments, when the stylet 230 is moved from its first position to its second position (i.e., when the distal end 233 of the stylet 230 is removed from the lumen 291 of the mesh carrier 290 and contacts the inner surface 219 of the elongate member 210), a user can hear an audible click.

Once in its second position, the stylet 230 is configured to decouple or otherwise disengage the mesh carrier 290 from the elongate member 210. Because the distal end portion 233 of the stylet 230 is configured to contact the proximal end portion 294 of the mesh carrier 290, when the stylet 230 is moved in a distal direction, it can advance the mesh carrier 290 in a distal direction out of the lumen 218 of the elongate member 210, thereby disengaging or decoupling the mesh carrier 290 from elongate member 210 and fixing it into bodily tissue. Specifically, the distal end portion 233 of the stylet 230 is configured to engage the mesh carrier 290 such that an orientation of a longitudinal axis A1-A1 defined by the mesh carrier 290 is substantially orthogonal to the longitudinal axis B 1-B 1 defined by the handle 270 coupled to the elongate member 210 (shown, for example, in FIG. 4).

The stylet 230 can be constructed of any material suitable for insertion into a body of a patient. For example, in some embodiment, the stylet can be constructed of stainless steel. In other embodiments, the stylet can be constructed of a polymer.

FIGS. 16 and 17 are side and perspective views, respectively, of a mesh carrier 290 that can be used with the insertion device 200 described above. The mesh carrier 290 has a proximal end portion 294, a distal end portion 293, defines a lumen 291 (shown in FIG. 19) extending between the proximal end portion 294 and the distal end portion 293, and defines an aperture 292. The proximal end portion 294 of the mesh carrier 290 is configured to engage or be removably coupled to at least a portion of the distal end portion 213 elongate member 210, shown, for example, in FIGS. 2-9, 18, and 19. In the illustrated embodiment, a portion of the proximal end portion 294 is configured to be disposed within the lumen 218 of the elongate member 210 (shown, for example, in FIGS. 18 and 19) such that the lumen 291 of the mesh carrier 290 is in communication with the lumen 218 of the elongate member 210. Said another way, the proximal end portion 294 of the mesh carrier 290 defines an opening 291a in communication with the lumen 291 of the mesh carrier 290. The opening 291a is in communication with the lumen 218 of the elongate member 210. Thus, the opening 291a, and thereby the lumen 291, are configured to receive the distal end portion 233 of the stylet 230 (shown in dashed lines in FIG. 16) from the elongate member 210.

Specifically, the mesh carrier 290 is coupled to the elongate member 210 by an interference or frictional fit. Although, the proximal end portion 294 of the mesh carrier 290 defines a substantially smooth outer surface, In other embodiments, the outer surface of the proximal end portion 294 can include a textured surface. For example, in some embodiments, the outer surface of the proximal end of the mesh carrier can include at least one rib or ridge (not shown) configured to help provide an interference or frictional fit with the lumen of the elongate member.

Figure 18:
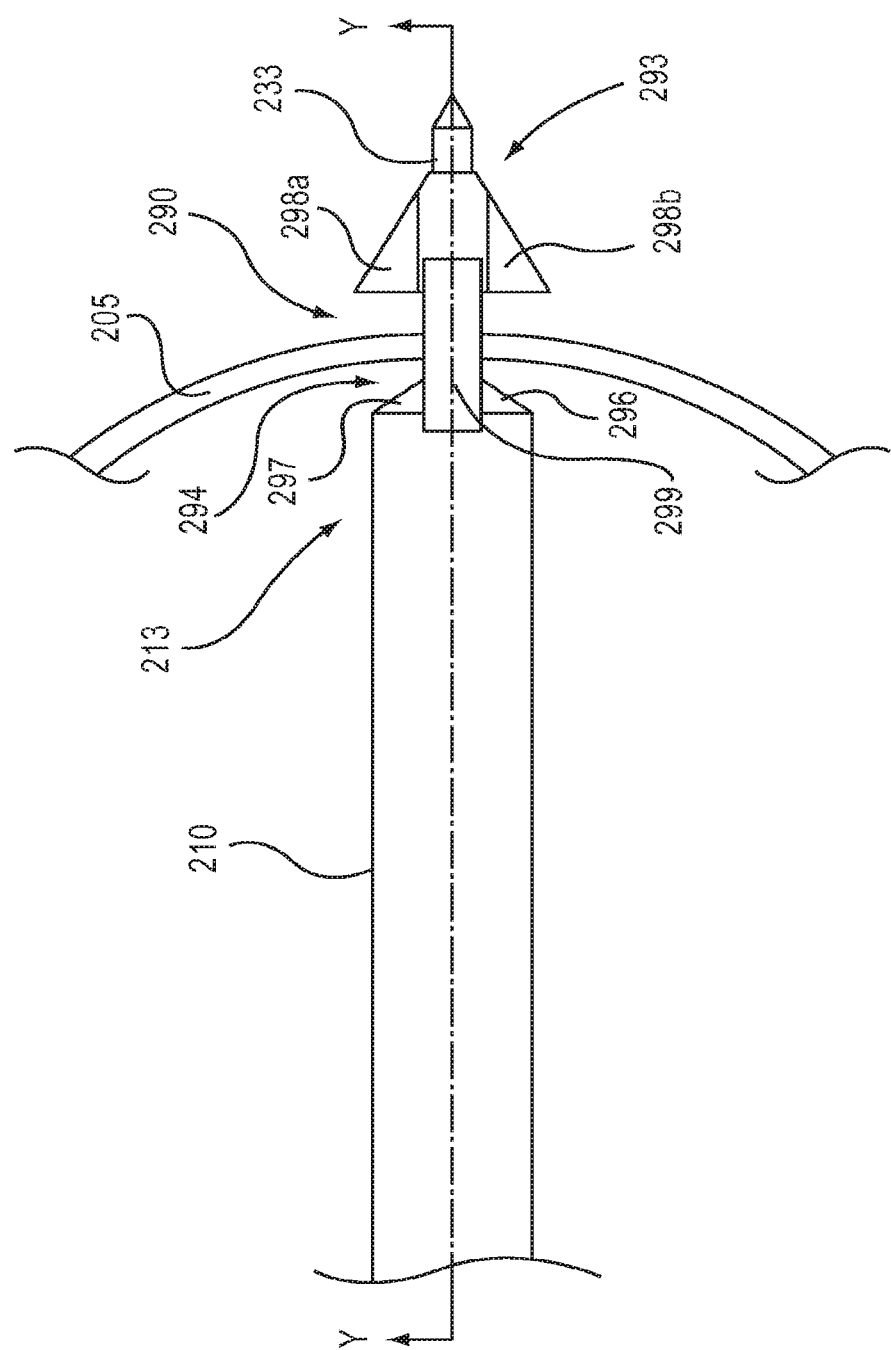
FIG. 18 is a side view of a distal end portion of the insertion device of FIG. 2 and a filament.
Figure 19:
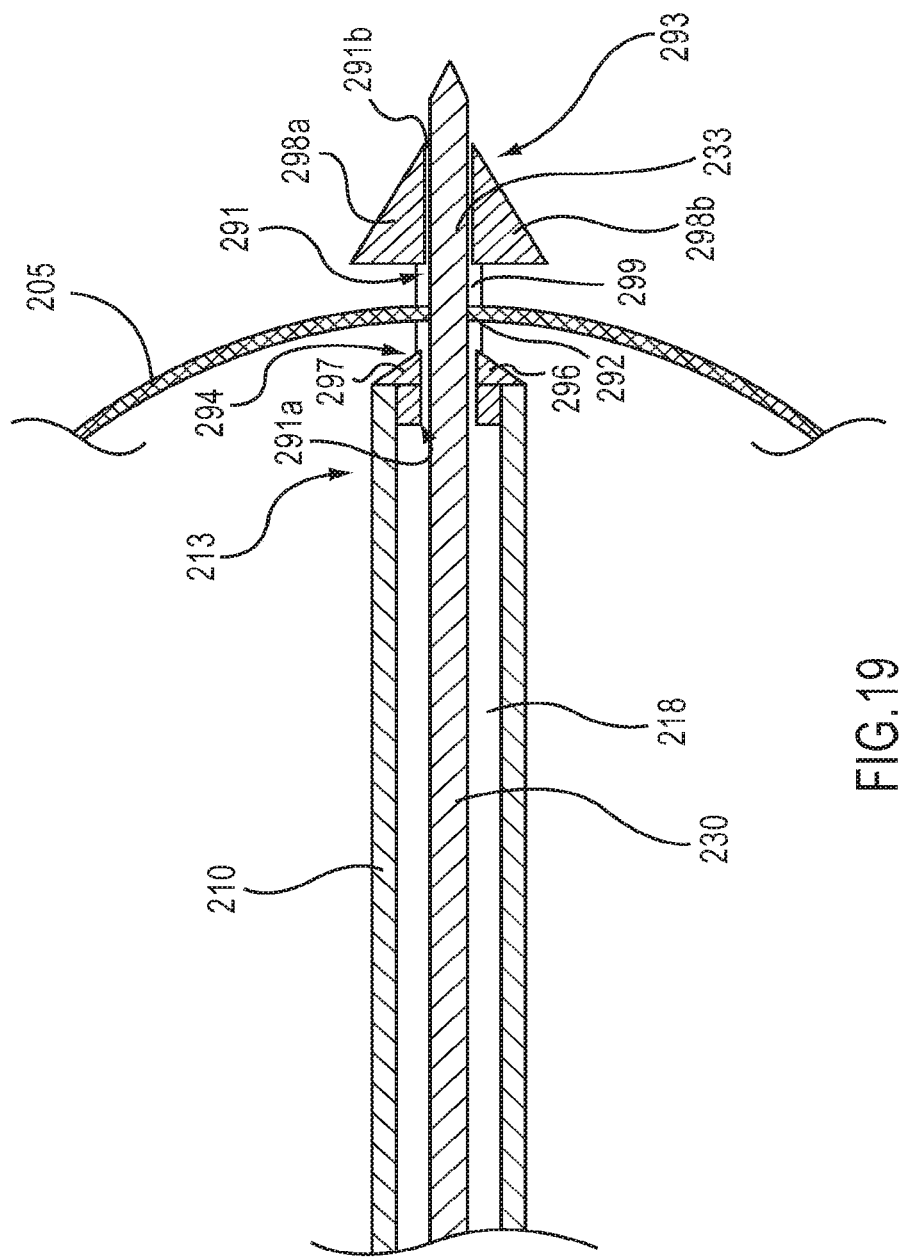
FIG. 19 is a cross-sectional view of the insertion device and filament of FIG. 18.

The proximal end portion 294 of the mesh carrier 290 includes protrusions 296, 297 disposed about a periphery of the mesh carrier 290 approximately 180 degrees apart (shown in FIGS. 16 and 17). In some embodiments, the protrusions 296, 297 are configured to contact the distal end portion 213 of the elongate member 210 when the mesh carrier 290 is coupled to the elongate member 210, as shown in FIGS. 18 and 19. Protrusions 296, 297 are further configured to help anchor at least a portion of the mesh carrier 290 in the body of the patient once the mesh carrier 290 is placed within the bodily tissue.

The proximal end portion 294 of the mesh carrier 290 further includes a first anchor portion 299 (shown, for example, in FIGS. 16 and 17) configured to help anchor the mesh carrier 290 in the bodily tissue of the patient once the mesh carrier 290 is placed within the bodily tissue. The first anchor portion 299 includes projections 299a and 299b disposed about the periphery of the proximal end portion 294 of the mesh carrier 290 approximately 180 degrees apart.

The distal end portion 293 of the mesh carrier 290 includes a second anchor portion 298 (shown, for example, in FIGS. 16 and 17) configured to help anchor at least a portion of the mesh carrier 290 in the body of the patient once the mesh carrier 290 is placed within the bodily tissue. The second anchor portion 298 includes projections 298a and 298b disposed about the periphery of the distal end portion 293 of the mesh carrier 290.

The first anchor portion 299 (i.e., projections 299a, 299b) and the second anchor portion 298 (i.e., projections 298a, 298b) are configured to help prevent the mesh carrier 290 from regressing through the bodily tissue in which it is placed. For example, in one application, the first anchor portion 299 and the second anchor portion 298 are configured to retain or anchor the mesh carrier 290 in one of the obturator internus or obturator externus muscles.

As illustrated in FIG. 19, the aperture 292 defined by the mesh carrier 290 is configured to receive at least a portion of the filament 205. The aperture 292 is configured to allow the filament 205 to be threaded or passed through the mesh carrier 290 via the aperture 292. The aperture 292 can be configured to allow movement or adjustment of at least a portion of the filament 205 through the aperture 292. For example, in some embodiments, the filament 205 can be movable through the aperture 292 in only a first direction (i.e. one way). In other embodiments, the filament 205 can be movable through the aperture 292 in the first direction and in a second direction that is different than the first direction. The aperture 292 can also be configured to provide little or no resistance to movement or adjustment of the filament 205. For example, the aperture 292 can have an opening greater in size than the width or thickness of the filament 205. In such an embodiment, the filament 205 can readily be moved through the aperture 292, meeting minimal or no resistance.

In one embodiment, the aperture 292 is configured to provide a frictional fit with the filament 205 passed through (or received within) the aperture 292. For example, the aperture 292 can be configured to be slightly smaller (or narrower) than the thickness of the filament 205. In such an embodiment, a force must be applied to move the filament 205 through the aperture 292. In yet another embodiment, the aperture 292 provides substantial resistance to movement or adjustment of the filament 205, such that the filament 205 is substantially fixed within the aperture 292.

The aperture 292 can have any suitable size or shape configured to receive the filament 205, for example the shape can be a U-shape (as illustrated in FIGS. 16 and 17), circle, square, rectangle star, triangle, trapezoid, or any other shape configured to receive a filament.

The mesh carrier 290 can be constructed of any material suitable for implantation into bodily tissue. For example, the mesh carrier 290 can be constructed of implantable grade polypropylene, implantable grade metal, a polymer, a biocompatible material, or any combination thereof. Suitable biocompatible materials include bioabsorbable, cadaveric, and bovine materials.

Although the mesh carrier 290 is illustrated and described as being received by the elongate member 210, it should be understood that other suitable configurations can be used. For example, the mesh carrier can be configured to receive a portion of the elongate member to couple the mesh carrier to the elongate member. Specifically, at least a portion of an outer surface of the elongate member can be configured to provide an interference or slight frictional fit with a mesh carrier when at least a portion of the elongate member is received in a lumen of the mesh carrier. Said another way, a portion of the mesh carrier can be configured to be disposed over a portion of the elongate member. In such an embodiment, the elongate member can include a sheath disposed about an outer surface of the elongate member for disengaging the mesh carrier (discussed in more detail below).

Although the mesh carrier 209 is illustrated and described above as defining a lumen 291 and an opening 291a configured to receive the distal end portion 233 of the stylet 230, other suitable configurations can be used. For example, the proximal end portion of the mesh carrier can define a substantially solid surface configured to contact the distal end portion of the stylet. Specifically, in such embodiments, the style is moved in a distal direction, such that the distal end portion of the stylet moves distally within the lumen of the elongate member and contacts the proximal end portion of the mesh carrier to decouple or otherwise disengage the mesh carrier from the elongate member.

Figure 20:
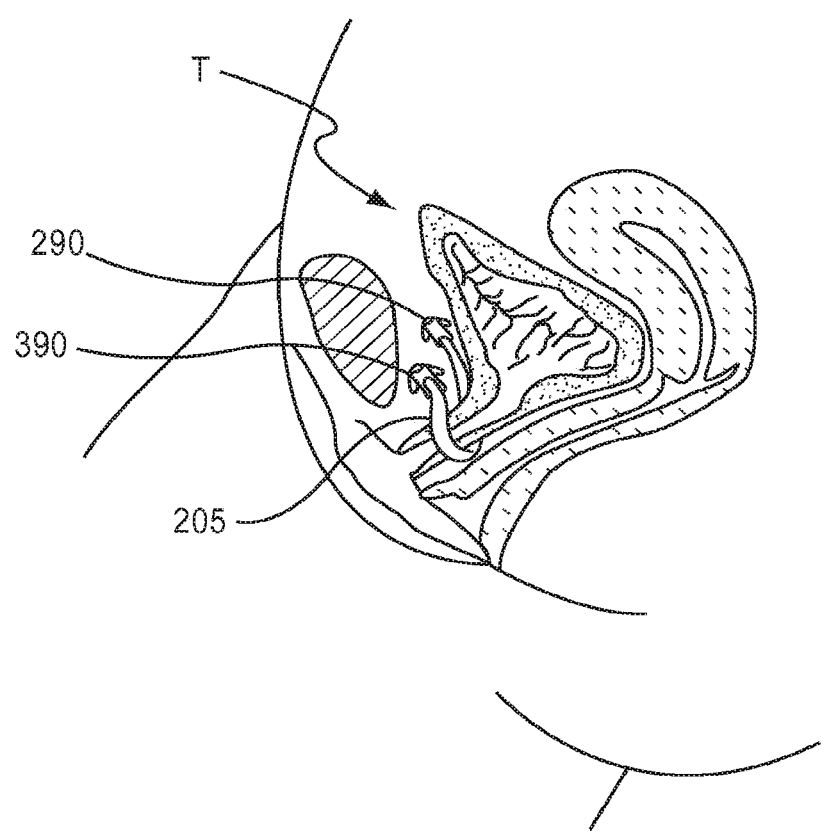
FIG. 20 is a side view of an embodiment of an implant positioned within a body of a patient.

In some embodiments, the insertion device 200 described above, can be used to insert a plurality of mesh carriers within bodily tissue of a patient. As shown in FIG. 20, the insertion device 200 can be used to insert a first mesh carrier 290 and a second mesh carrier 390 into bodily tissue T of a patient. FIG. 20 illustrates an example of the first mesh carrier 290 and the second mesh carrier 390 anchored in bodily tissue T of the pelvic region of a patient. The filament 205 extends between the first mesh carrier 290 and the second mesh carrier 390 to provide support to the target tissue T or organ. In the illustrated embodiment, the filament 205 extends below the urethra and forms a sling to provide support to the urethra.

The filaments and implants as discussed above can be constructed of many different suitable materials and have many different suitable configurations. For example, in some embodiments, a polymer mesh implant is used, which can be used to support the urethra. In other embodiments, a polyform material can be used.

In some embodiments, a portion of the filament can be reinforced, such as with a reinforcing material. The reinforcing material, or reinforced portion of the filament, can be configured to assist in suspending or supporting the bodily tissue or organ. In one embodiment, the filament can be reinforced by a suture.

In some embodiments, at least a portion of the filament can include tangs or a tanged portion to grip or attach to a portion of bodily tissue. The terms "tanged" or "tangs" as used herein mean roughened or jagged edges or areas, such as can result from cutting a woven or knit mesh material or filament. The tangs enhance anchoring of the filament within bodily tissue, such as pubo-urethral tissue. In one embodiment, the filament includes tangs on an edge along an entire length of the filament. In another embodiment, tangs are only on the end portions of the filament.

In other embodiments, the filament is untanged or detanged, such as by heating the tangs on a polymer mesh so that they fuse and bead up to form a smooth finish.

In some embodiments, the filament includes a coating. For example, the filament can include a polymeric coating. In another example, the filament can include a therapeutic agent coating.

In yet other embodiments, the filament can be porous. A porous filament defines openings, or pores, in the filament or between threads of material forming the filament. For example, in one embodiment, the filament is a mesh. The filament can be a micro-porous mesh in which the openings, or pores, are small.

Figure 21:
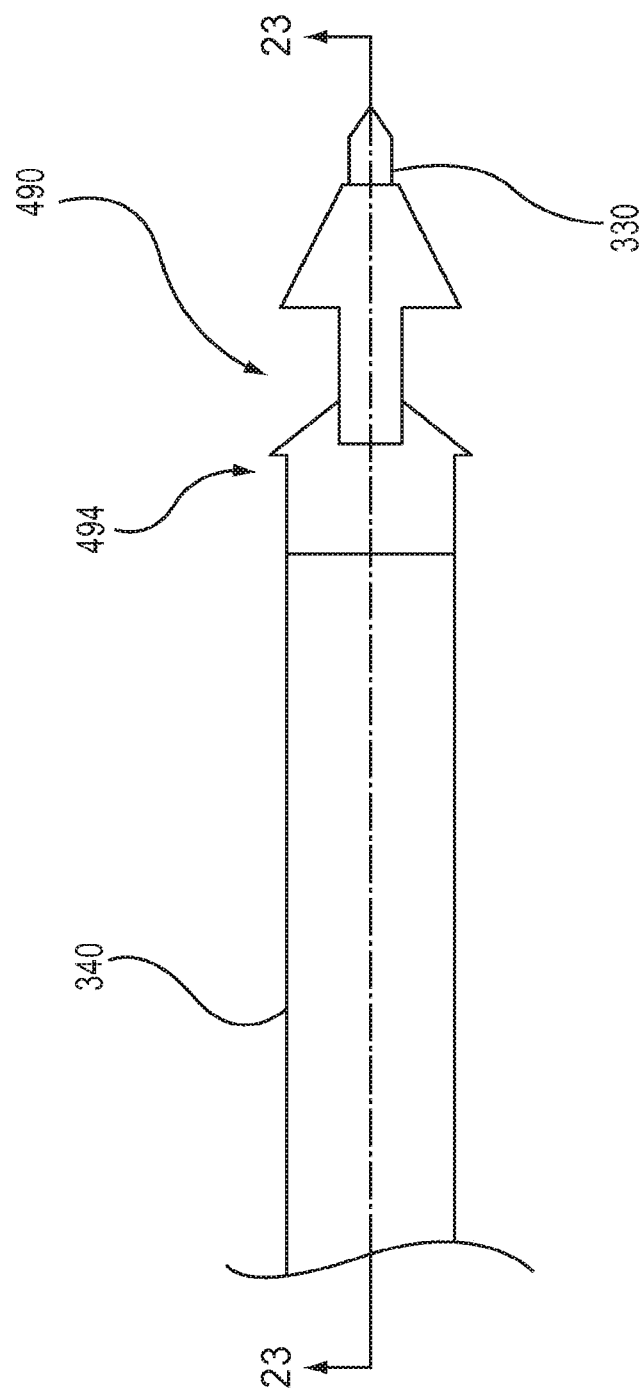
FIG. 21 is a side view of an distal end portion of the insertion device according to another embodiment.
Figure 22:
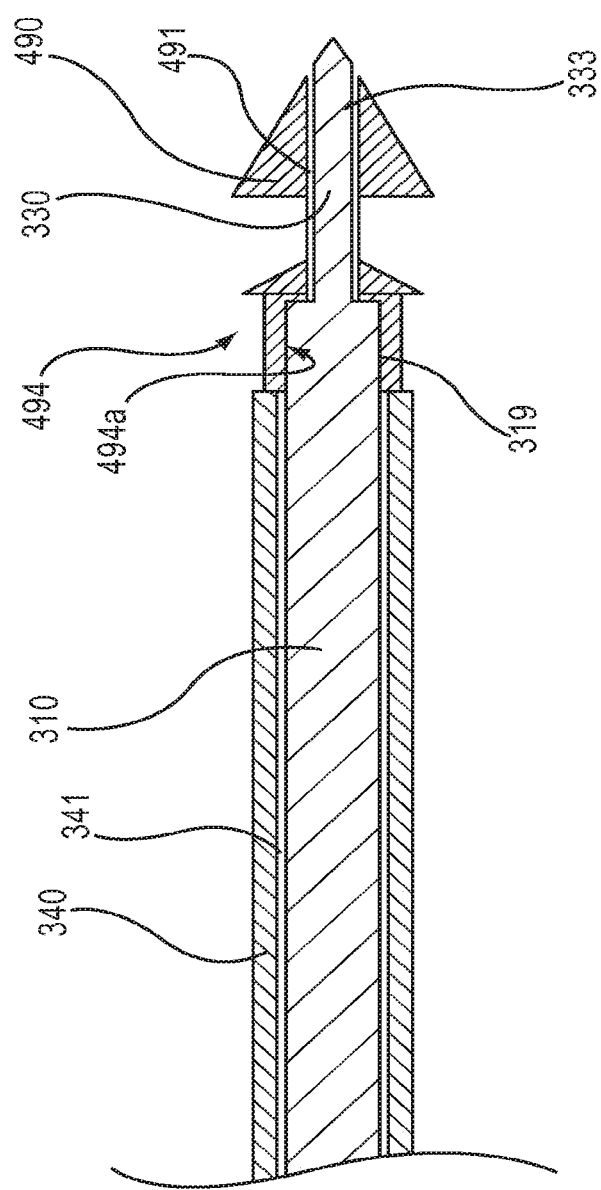
FIG. 22 is a cross-sectional view of the insertion device of FIG. 21 along line 23-23 with a stylet in a first position.
Figure 23:
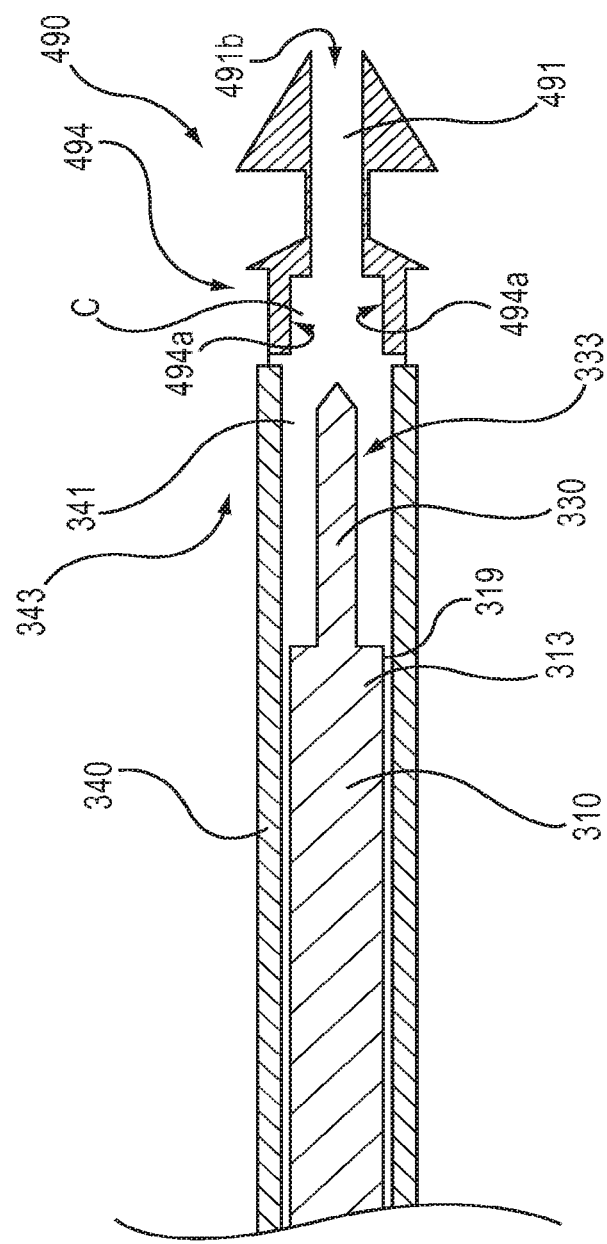
FIG. 23 is a cross-sectional view of the insertion device of FIG. 21 along line 23-23, with a stylet in a second position.

Although the stylet 230 as illustrated in FIGS. 2-15, 18, and 19 is slidably disposed within the lumen 218 of the elongate member 210, it should be understood that other configurations are possible. As shown in FIGS. 21-23, the stylet 330 can be fixedly retained within the elongate member 310. For example, the elongate member 310 and the stylet 330 can be formed as one component such that they do not move relative to one another. In such embodiments, the elongate member 310 is slidably disposed within a lumen 341 defined by a sheath 340. Said another way, the sheath 340 is slidably disposed about an outer surface 319 of the elongate member 310 for disengaging the mesh carrier 490 from the elongate member 310.

The proximal end portion 494 of the mesh carrier 490, in such embodiments, defines a cavity C configured to receive at least a portion the distal end portion 313 of the elongate member 310. Specifically, an inner surface 494a of the proximal end portion 494 of the mesh carrier 490, which defines the cavity C is configured to provide an interference or slight frictional fit with an outer surface 319 of the elongate member 310 received in the cavity C. In such embodiments, when the stylet 330 (and elongate member 310) is in its first configuration, the stylet 230 is configured such that a portion of the distal end portion 333 the stylet 330 extends through the lumen 491 of the mesh carrier 490 and out the opening 491b, as shown in FIGS. 21 and 22. As the stylet 330 moves proximally with respect to the sheath 340 from its first position to its second position, the distal end portion 343 of the sheath 340 contacts a portion of the proximal end portion 494 of the mesh carrier 490 and prevents proximal movement of the mesh carrier 490. When the stylet 330 is in its second position, as illustrated, for example, in FIG. 23, the elongate member 310 and the distal end portion 333 of the stylet 330 is disposed within the lumen 341 of the sheath 340. Specifically, in the illustrated embodiment, when the stylet 330 is moved proximally from its first position, the distal end portion 343 of the sheath 340 contacts the proximal end portion 494 of the mesh carrier 490 maintaining its location within bodily tissue. The mesh carrier 490 is thereby decoupled or removed from the distal end portion 313 of the elongate member 310 and is released in bodily tissue.

In some embodiments, an inner surface of the proximal end 494 of the mesh carrier 490 can include at least one rib or ridge configured to help provide the interference or frictional fit with the outer surface 319 of the elongate member 310.

Although the insertion devices are illustrated and described above as including an elongate member having a radius of curvature such that the proximal end portion of the elongate member defines an axis substantially orthogonal to an axis defined by the distal end portion of the elongate member, other suitable configurations can be used. For example, the axis defined by the proximal end portion of the elongate member and the axis defined by the distal end portion of the elongate member can define an angle greater than or less than 90 degrees relative to one another.

Figure 24:
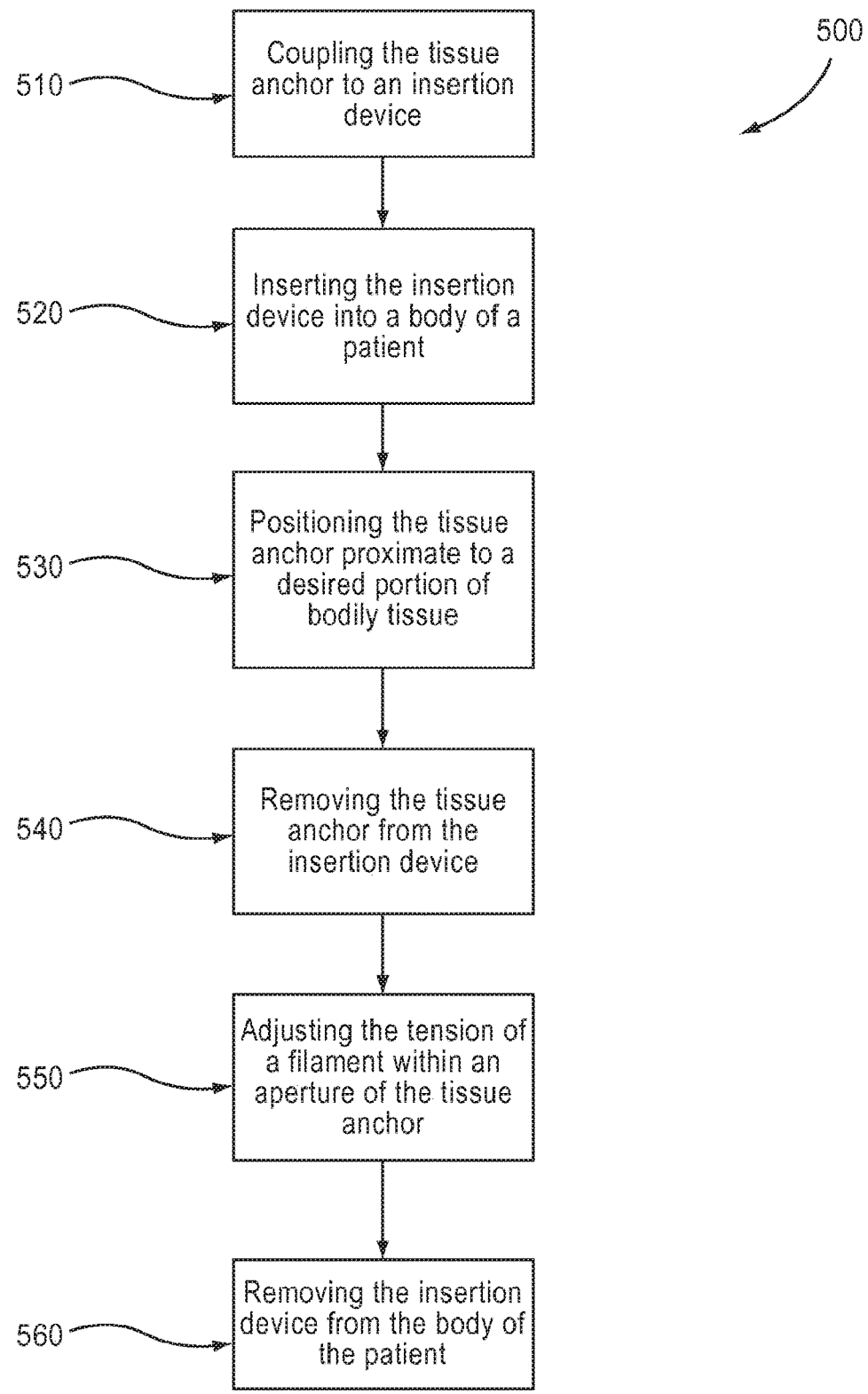
FIG. 24 is a flowchart of a method according to an embodiment.

FIG. 24 is a flowchart of a method 500 for delivering a mesh carrier into bodily tissue of a patient using a insertion device according to an embodiment of the invention.

At 510, the mesh carrier is coupled to the stylet of the insertion device. For example, the proximal end portion of the mesh carrier is engaged with the distal end portion of the elongate member. For example, in some embodiments, a portion of the proximal end portion of the mesh carrier is received within the lumen defined by the distal end portion of the elongate member. In other embodiments, the portion of the proximal end portion of the mesh carrier is configured to receive a portion of the distal end portion of the elongate member.

In some embodiments at least a portion of the filament is inserted into the aperture defined by the mesh carrier prior to the coupling of the mesh carrier to the elongate member. For example, at least a portion of the filament is inserted into the aperture such that at least a portion of the filament is substantially orthogonal to the lumen defined by the mesh carrier.

In some embodiments, the mesh carrier is coupled to or engaged with the elongate member when the stylet is in its first position. In such embodiments, the stylet passes through the filament inserted into the aperture defined by the mesh carrier and retains the filament within the aperture of the mesh carrier.

At 520, the insertion device is inserted into a body of a patient. For example, in one embodiment, the insertion device is inserted into the body of the patient through an incision made in bodily tissue. In a procedure for urinary incontinence, one approach for inserting the insertion device into the body of the patient includes making an incision in the vaginal wall and inserting a portion of the insertion device through the vaginal incision. The portion of the insertion device is then directed towards the desired bodily tissue. The curved elongate member is useful in navigating around certain bodily structures to reach the desired bodily tissue.

At 530, the mesh carrier is positioned proximate to a desired portion of bodily tissue, and the mesh carrier is inserted into the bodily tissue. For example, in a procedure for female urinary incontinence, the mesh carrier is inserted into one of the obturator intern us or obturator externus muscles.

At 540, the mesh carrier is removed from the lumen at the distal end portion of the elongate member. Specifically, the stylet is moved from its first position to its second position, and then from its second position to its first position. For example, in one embodiment, as shown in FIG. 7, the stylet is moved in a proximal direction, from its first position to its second position, such that the distal end portion of the stylet is withdrawn from the lumen of the mesh carrier and the filament. By withdrawing the distal end portion of the stylet from the lumen of the mesh carrier and disposing it within the lumen of the elongate member, the distal end portion of the stylet becomes offset from an axis defined by the distal end portion of elongate member and contacts the inner wall of the elongate member. The distal end portion of the stylet is configured to contact a portion of the proximal end portion of the mesh carrier when in its second configuration. In one procedure, a practitioner concurrently pulls the handle in a proximal direction while holding the coupling member substantially stationary. In another procedure, the practitioner concurrently pushes the coupling member in a distal direction, thereby moving the elongate member in a distal direction, while holding the handle substantially stationary.

To remove the mesh carrier, the stylet is moved in a distal direction from its first position to its second position such that the distal end portion of the stylet concurrently moves the mesh carrier in a distal direction thereby removing the mesh carrier from the lumen at the distal end portion of the elongate member. Thus, the mesh carrier is decoupled from the elongate member, and the mesh carrier and filament are fixed within the bodily tissue.

At 550, the filament is moved, or adjusted, through the aperture of the mesh carrier. In one embodiment, the filament is moved or adjusted through the aperture in a first direction. For example, the filament is moved in the first direction to increase tension in the filament. In another example, the filament is moved in the first direction to decrease the length of the filament, for example, to shorten the length of the filament that will support or suspend a target organ or tissue.

In some embodiments, the filament is moved, or adjusted, through the aperture in a second direction different than the first direction. For example, the filament is moved in the second direction to decrease the tension in the filament. In one embodiment, the filament is moved in the second direction to increase the length of the filament suspended between a first mesh carrier and a second mesh carrier. For example, the filament is moved in the second direction to alter the position of the organ or tissue being supported or suspended, such as by increasing the length of filament between a first mesh carrier and a second mesh carrier and lowering the organ or tissue to a more anatomically correct position.

In another example, the filament is moved in the second direction to create or increase a space between the filament and the organ or tissue to be supported or suspended. For example, in a treatment for urinary incontinence, the filament can be adjusted to leave a space between the filament and the urethra (the organ to be supported). The space exists between the filament and the urethra when the patient is in one position. When the patient moves to another position, such as an upright position, the urethra shifts to occupy the space and is then supported by the filament.

In one embodiment, the filament is manually moved by a practitioner. In another embodiment, the practitioner grips at least a portion of the filament with a medical instrument, such as forceps, to move the filament.

Adjustment of the filament through the aperture in the first direction or in the second direction different than the first direction can be repeated until the desired tension or length of filament is achieved. For example, a practitioner can alternatively move the filament in the first direction to increase tension and move the filament in the second direction to decrease tension until the desired tension is achieved.

In some embodiments, the filament can be trimmed to a preferred length once the desired tension is achieved or once the mesh carrier is disengaged from the elongate member and delivered into bodily tissue.

At 560, the insertion device is withdrawn from the body of the patient.

Although activities of a method of delivering a mesh carrier into bodily tissue have been illustrated and described in one order, each activity is not required for delivery of a mesh carrier into bodily tissue. For example, in some embodiments, the filament can be adjusted in only one direction through the aperture of the mesh carrier. In another example, the filament is not adjusted through the aperture of the mesh carrier at all.

A method for delivering a mesh carrier (and filament or implant) into bodily tissue of a patient can include delivering more than one mesh carrier for securing a filament to bodily tissue. For example, in one embodiment, as illustrated in FIG. 20 two mesh carriers are delivered into bodily tissue of the patient. Alternatively, three, four, or more mesh carriers are delivered into bodily tissue of the patient). In an embodiment with two or more mesh carriers, the first mesh carrier is delivered as described above. It is not necessary, however, to adjust the filament received within the aperture of the first mesh carrier. The length or tension of the filament can be adjusted with regard to any one or more of the second, third, fourth, or more mesh carriers. The length between fixed mesh carriers can be any suitable length. For example, the length between fixed mesh carriers can be about 8 centimeters, 10 centimeters, 12 centimeters, 14 centimeters, 16 centimeters, or longer or shorter. In an embodiment with two or more mesh carriers, each mesh carrier is delivered in a substantially similar manner as described above with respect to the first mesh carrier. For ease of operation, the filament can be inserted into the aperture of each mesh carrier before the first mesh carrier is delivered into bodily tissue.

Figure 25:
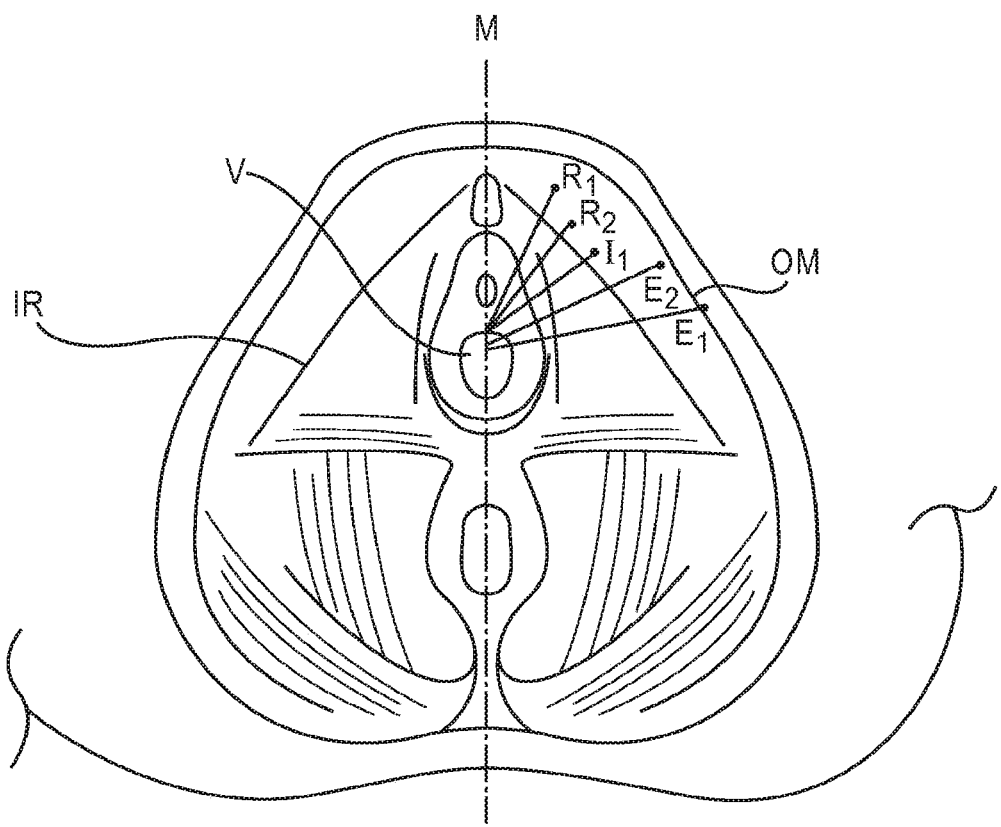
FIGS. 25-27 illustrate locations within the female pelvic region in which an insertion device can be inserted.
Figure 26:
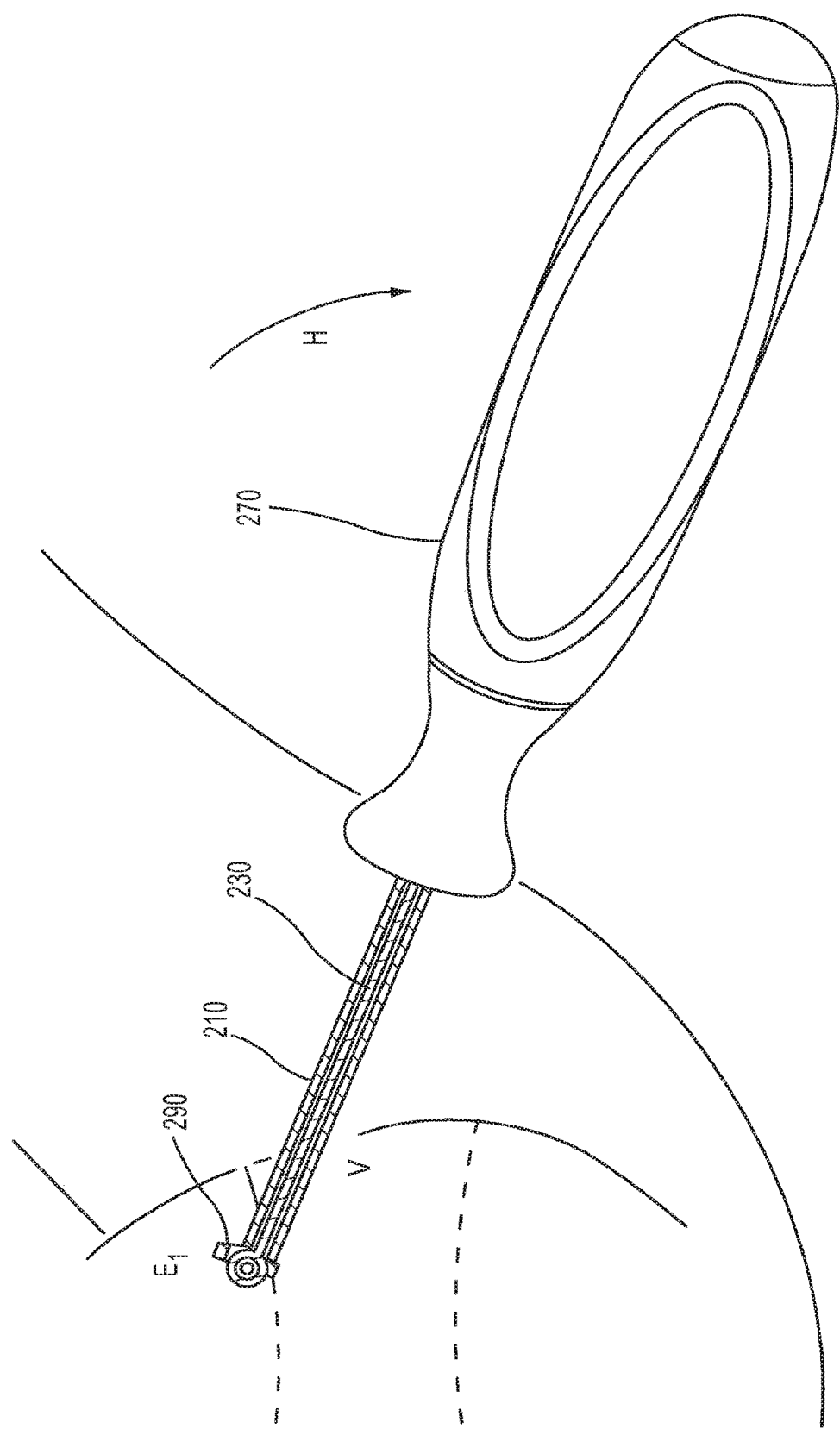
Figure 27:
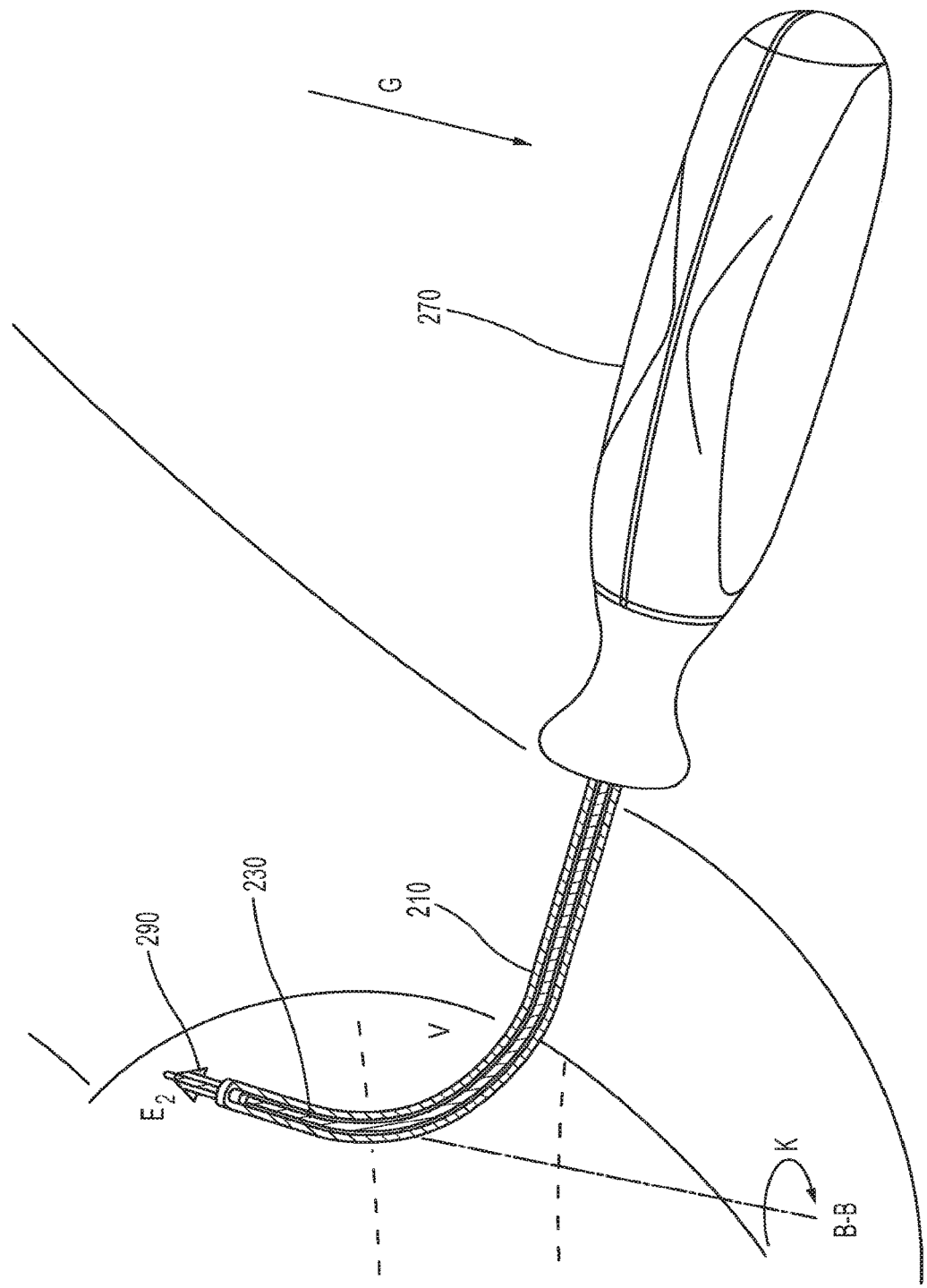

FIGS. 25-27 illustrate locations within the female pelvic region in which an implant can be placed using the method of delivery as discussed above with respect to FIG. 24. In some embodiments, as illustrated in FIG. 25, an implant can be placed within the body through the obturator membrane and into the externus muscle as indicated by $E_1$ and $E_2$. By inserting the insertion device through the obturator membrane and into the externus muscle, the insertion device can be directed in a lateral direction to form a hammock configuration. Specifically, by fixing the implant (i.e., mesh carriers, filament, etc.) in the $E_1$ location (shown in FIG. 26) and the contra lateral side, the implant will form the hammock configuration. In some embodiments, the hammock configuration can be achieved by placing the mesh carriers in a muscle at a location $I_1$. Alternatively, the insertion device can be moved in a direction toward a shoulder blade of a patient to provide a "U" shaped configuration. Specifically, by fixing the implant in the $E_2$ location (shown in FIG. 27) and the contra lateral side, the implant will form the "U" shaped configuration.

Although the "U" shaped implant is achieved when placed within the body through the obturator membrane and into the externus muscle, the "U" shaped implant configuration, however, can also be achieved via a retro-pubic approach by placing the mesh carriers at the locations marked R1 and R2.

Figure 4:
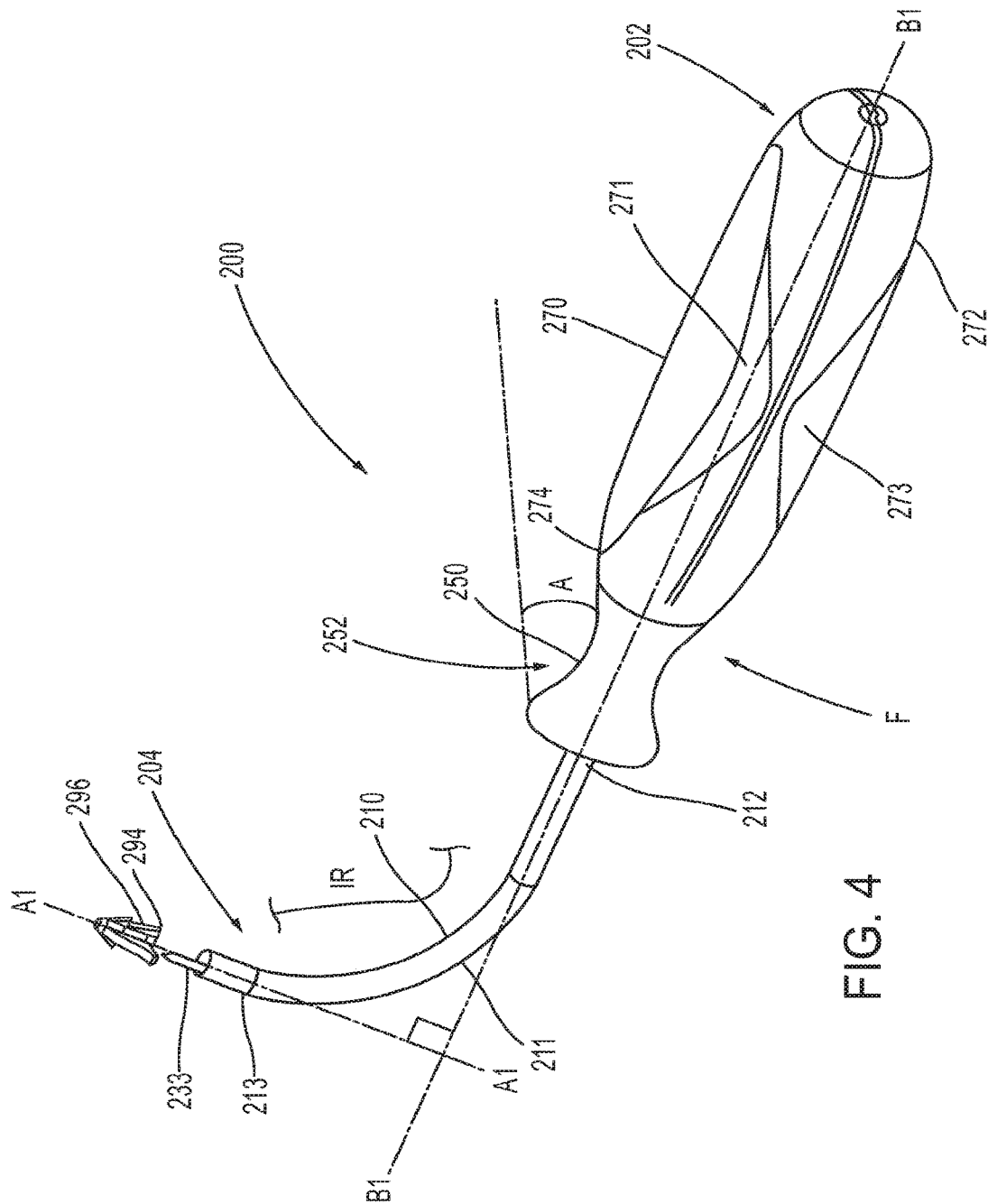
FIG. 4 is a side perspective view of the insertion device of FIG. 2 with the stylet removing the mesh carrier.

When fixing the implant to tissue, an insertion device (for example, insertion device 200, including stylet 230 and mesh carrier 290, as discussed above with respect to FIGS. 2-19), is inserted through the vagina V and is advanced along and around the ischiopubic ramus IR, shown in FIG. 4, until the tip of the stylet is proximate the obturator membrane. The handle of the insertion device is rotated, in either the C direction or the D direction (shown in FIG. 15) such that the tip of the stylet 230 of the insertion device 200 is aimed at the desired tissue. The handle can also be pivoted in a direction H (shown in FIG. 26). Alternatively, the tip of the stylet 230 of the insertion device 200 can be aimed by pivoting the handle 270 to a location A, as shown in FIG. 4. The handle 270 is then pivoted such that the axis B1-B1 defined by the handle 270 (shown, for example, in FIG. 4) is parallel to the midline M of the patient (shown in FIG. 25). A force in a direction F (shown in FIGS. 4 and 27) is applied to the handle 270 such that the tip of the stylet 230 and the mesh carrier 290 is advanced through the obturator membrane OM and into the externus muscle, and such that the axis B1-B1 remains substantially parallel to the midline M of the patient. The elongate member 210 of the insertion device 200 contacts the ischiopubic ramus IR (shown in FIG. 4) such that it prevents further lateral movement of the stylet tip into the externus muscle.

In one embodiment, as shown in FIG. 26, the mesh carrier 290 is inserted in the E1 location. In such an embodiment, a force of gravity G due to a weight of the handle 270 causes the handle 270 to rotate in a direction H such that inadvertent removal of the mesh carrier 290 due to the weight of the handle 270 is unlikely. In another embodiment, as shown in FIG. 27, the mesh carrier 290 is inserted in the E2 location. In this instance, the force of gravity G can cause the handle 270 to pivot such that the axis B1-B1 defined by the handle 270 is substantially offset from the midline M of the patient. The force of gravity G can also cause the handle 270 to rotate in a direction K about axis B-B defined by the distal end portion of the elongate member 210 of the insertion device 200. In such an embodiment, the force of gravity G due to the weight of the handle 270 can affect the holding strength of the mesh carrier 290. Therefore, in some embodiments, the possibility of inadvertent removal of the mesh carrier 290 can be reduced. For example, in such embodiments, the cavity defined by the handle 270, as discussed in detail above, can be defined such that the handle 270 has a minimal weight.

In one embodiment, an insertion device includes an elongate member having a proximal end portion, a distal end portion, and defining a lumen therethrough. The elongate member includes a curved portion between the proximal end portion and the distal end portion. The distal end portion is configured to be removably coupled to a mesh carrier. The proximal end portion includes a handle defining a longitudinal axis. The insertion device also includes a stylet that has a proximal end portion, a distal end portion and is configured to move from a first position to a second position with respect to the elongate member. The stylet is configured to engage the mesh carrier to remove the mesh carrier from the elongate member such that a longitudinal axis defined by the mesh carrier is substantially orthogonal to the longitudinal axis defined by the handle.

In one embodiment, the distal end portion of the stylet is configured to extend outside of the distal end portion of the elongate member when the stylet is in its first position. In another embodiment, the distal end portion of the stylet is configured to contact a proximal end portion of a mesh carrier when the stylet is moved from its second position to its first position.

In one embodiment, a longitudinal axis defined by the proximal end portion of the elongate member is substantially orthogonal to a longitudinal axis defined by the distal end portion of the elongate member. In another embodiment, the curved portion of the elongate member has a radius of curvature of approximately 1.1 inches.

In one embodiment, the lumen of distal end portion of elongate member is configured receive a portion of the mesh carrier and to provide an interference fit with the mesh carrier.

In one embodiment, the elongate member includes stainless steel. In another embodiment, the handle is slidably coupled to the proximal end portion of the elongate member and the handle has at least one groove. The proximal end of the elongate member includes a coupling member that has at least one protrusion configured to engage the at least one groove.

In one embodiment, the insertion device includes a coupling member coupled to the proximal end portion of the elongate member. The coupling portion defines at least one protrusion.

In another embodiment, the insertion device includes a coupling member coupled to the proximal end portion of the elongate member. The coupling member includes a coupling portion extending proximally therefrom. The coupling portion defining at least one protrusion. The handle is configured to engage the at least one protrusion of the coupling portion.

In another embodiment, an insertion device includes an elongate member having a proximal end portion, a distal end portion, and defining a lumen therethrough. An axis defined by the proximal end portion of the elongate member is substantially orthogonal to an axis defined by the distal end portion of the elongate member. The insertion devise also includes a stylet having a proximal end portion and a distal end portion. At least a portion of the stylet is disposed within the lumen of the elongate member. The stylet is slidably coupled to the elongate member such that the stylet is configured to move from a first position to a second position with respect to the elongate member.

In one embodiment, the elongate member includes a curved portion that has a radius of curvature of 1.1 inches.

In another embodiment, the distal end portion of the elongate member is configured to be removably coupled to a mesh carrier. In yet another embodiment, the lumen defined by the elongate member is configured to receive a portion of a mesh carrier and to provide an interference fit with the mesh carrier.

In one embodiment, the stylet is biased to a linear configuration.

In another embodiment, the insertion device also includes a coupling member disposed about the proximal end portion of the elongate member. The coupling member has at least one protrusion. The handle has at least one groove to engage the at least one protrusion of the coupling member.

In one embodiment, the elongate member includes stainless steel.

In one embodiment, the distal end portion of the stylet is configured to pierce a filament received in a mesh carrier when the insertion device is in its first configuration. In another embodiment, the distal end portion of the stylet is configured to decouple a mesh carrier from the elongate member when the stylet is moved from its second position to its first position.

A method of inserting a mesh carrier into a body of a patient includes (1) coupling the mesh carrier to a distal end portion of an elongate member of an insertion device; (2) inserting the insertion device into the body; (3) decoupling the mesh carrier such that a longitudinal axis defined by the mesh carrier is substantially orthogonal to an axis defined by the proximal end portion of the elongate member; and (3) removing the insertion device from the body.

In one embodiment, the coupling of the mesh carrier includes moving the stylet to its first position such that a distal end portion of a stylet extends beyond the distal end portion of the elongate member. In another embodiment, the decoupling of the mesh carrier includes moving the stylet from its first position to a second position. In yet another embodiment, the moving of the stylet to its second position includes moving the stylet in a proximal direction.

In one embodiment, the method includes inserting a filament into an aperture defined by the mesh carrier prior to coupling the mesh carrier to the stylet. In another embodiment, the method includes inserting a filament into an aperture defined by the mesh carrier prior to coupling the mesh carrier to the stylet.

In one embodiment, the decoupling of the mesh carrier includes moving the stylet from its second position to its first position such that the distal end of the stylet contacts a proximal end portion of the mesh carrier. In another embodiment, the moving of the stylet to its first position includes moving the stylet in a distal direction.

In one embodiment, the method includes coupling a second mesh carrier to the distal end portion of the elongate member when the stylet is in its first position and inserting the insertion device into the body of the patient. In another embodiment, the method includes moving the stylet from its second position to its first position to decouple the second mesh carrier at a second location, wherein an orientation of the second mesh carrier is orthogonal to the axis defined by the proximal end of the elongate member, and removing the insertion device from the body.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The previous description of the embodiments is provided to enable any person skilled in the art to make or use the invention. While the invention has been particularly shown and described with reference to embodiments thereof, it will be understood by those skilled in art that various changes in form and details may be made. For example, a delivery instrument can include various combinations and sub-combinations of the various embodiments described herein.

What is claimed is:

1. An insertion device, comprising:
   an elongate member having a proximal end portion, a distal end portion, and defining a lumen therethrough, the elongate member including a curved portion between the proximal end portion and the distal end portion, the distal end portion configured to removably couple a tissue anchor thereto, the proximal end portion including a handle defining a longitudinal axis; and a stylet having a proximal end portion and a distal end portion, the stylet being configured to move from a first position to a second position with respect to the elongate member, and when the stylet is in the second position, the distal end portion of the stylet defines a longitudinal axis that is offset from a longitudinal axis defined by the distal end portion of the elongate member, the stylet configured to engage the tissue anchor to remove the tissue anchor from the elongate member such that a longitudinal axis defined by the tissue anchor is substantially orthogonal to the longitudinal axis defined by the handle.

2. The insertion device of claim 1, wherein the distal end portion of the stylet is configured to extend outside of the distal end portion of the elongate member when the stylet is in its first position.

3. The insertion device of claim 1, wherein the distal end portion of the stylet is configured to contact a proximal end portion of a tissue anchor when the stylet is moved from its second position to its first position.

4. The insertion device of claim 1, wherein a longitudinal axis defined by the proximal end portion of the elongate member is substantially orthogonal to a longitudinal axis defined by the distal end portion of the elongate member.

5. The insertion device of claim 1, wherein the curved portion of the elongate member has a radius of curvature of approximately 1.1 inches.

6. The insertion device of claim 1, the handle being slidably coupled to the proximal end portion of the elongate member, the handle having at least one groove, the proximal end of the elongate member includes a coupling member having at least one protrusion configured to engage the at least one groove.

7. The insertion device of claim 1, further comprising:
a coupling member coupled to the proximal end portion of the elongate member, the coupling member including a coupling portion extending proximally therefrom, the coupling portion defining at least one protrusion, wherein the handle is configured to engage the at least one protrusion of the coupling portion.

8. An insertion device, comprising:
an elongate member having a proximal end portion, a distal end portion, and defining a lumen therethrough, wherein an axis defined by the proximal end portion of the elongate member is substantially orthogonal to an axis defined by the distal end portion of the elongate member; and a stylet having a proximal end portion and a distal end portion, at least a portion of the stylet disposed within the lumen of the elongate member, the stylet being slidably coupled to the elongate member such that the stylet is configured to move from a first position to a second position with respect to the elongate member, and when the stylet is in the second position, the distal end portion of the stylet defines a longitudinal axis that is offset from a longitudinal axis defined by the distal end portion of the elongate member.

9. The insertion device of claim 8, the distal end portion of the elongate member is configured to be removably coupled to a tissue anchor.

10. The insertion device of claim 8, wherein the stylet is biased to a linear configuration.

11. The insertion device of claim 8, further comprising:
coupling member disposed about the proximal end portion of the elongate member, the coupling member having at least one protrusion, the handle having at least one groove to engage the at least one protrusion of the coupling member.

12. The insertion device of claim 8, wherein the distal end portion of the stylet is configured to pierce a filament received in a tissue anchor when the insertion device is in its first configuration.

13. A method of inserting a tissue anchor into a body of a patient, comprising:
coupling the tissue anchor to a distal end portion of an elongate member of an insertion device, the coupling of the tissue anchor includes extending a stylet through a filament coupled to the tissue anchor;
inserting the insertion device into the body;
decoupling the tissue anchor such that a longitudinal axis defined by the tissue anchor is substantially orthogonal to an axis defined by the proximal end portion of the elongate member; and
removing the insertion device from the body.

14. The method of claim 13, wherein the coupling of the tissue anchor includes moving the stylet to its first position such that a distal end portion of a stylet extends beyond the distal end portion of the elongate member.

15. The method of claim 13, wherein the decoupling of the tissue anchor includes moving the stylet from its first position to a second position.

16. The method of claim 13, further comprising:
inserting a filament into an aperture defined by the tissue anchor prior to coupling the tissue anchor to the stylet.

17. The method of claim 13, wherein the decoupling of the tissue anchor includes moving the stylet from its second position to its first position such that the distal end of the stylet contacts a proximal end portion of the tissue anchor.

18. The method of claim 13, wherein the moving of the stylet to its first position includes moving the stylet in a distal direction.

19. The method of claim 13, further comprising:
coupling a second tissue anchor to the distal end portion of the elongate member when the stylet is in its first position; and
inserting the insertion device into the body of the patient.

20. The method of claim 13, further comprising:
moving the stylet from its second position to its first position to decouple the second tissue anchor at a second location, wherein an orientation of the second tissue anchor is orthogonal to the axis defined by the proximal end of the elongate member; and
removing the insertion device from the body.

* * * * *